US011369675B2

(12) United States Patent
Taubenberger et al.

(10) Patent No.: US 11,369,675 B2
(45) Date of Patent: Jun. 28, 2022

(54) BROADLY PROTECTIVE INACTIVATED INFLUENZA VIRUS VACCINE

(71) Applicant: The U.S.A., as represented by the Secretary, Department of Health and Human Services, Bethesda, MD (US)

(72) Inventors: Jeffery Karl Taubenberger, Springfield, VA (US); Louis Merican Schwartzman, Olney, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 6 days.

(21) Appl. No.: 16/963,718

(22) PCT Filed: Jan. 18, 2019

(86) PCT No.: PCT/US2019/014220
§ 371 (c)(1),
(2) Date: Jul. 21, 2020

(87) PCT Pub. No.: WO2019/143955
PCT Pub. Date: Jul. 25, 2019

(65) Prior Publication Data

US 2021/0093711 A1 Apr. 1, 2021

Related U.S. Application Data

(60) Provisional application No. 62/620,051, filed on Jan. 22, 2018.

(51) Int. Cl.
*A61K 39/145* (2006.01)
*A61K 39/00* (2006.01)

(52) U.S. Cl.
CPC .... *A61K 39/145* (2013.01); *A61K 2039/5252* (2013.01); *A61K 2039/543* (2013.01)

(58) Field of Classification Search
CPC .................. A61K 39/145; A61K 39/12; A61K 2039/545; A61K 2039/5252; A61K 2039/70; A61K 39/295; C12N 2760/16111; A61P 31/16; C07K 16/1018; C07K 16/00; G01N 2333/11; G01N 33/68; A61M 2202/30
See application file for complete search history.

(56) References Cited

U.S. PATENT DOCUMENTS

| | | | | |
|---|---|---|---|---|
| 4,522,809 | A | 6/1985 | Adamowicz et al. | |
| 5,698,432 | A | 12/1997 | Oxford | |
| 9,278,127 | B2 * | 3/2016 | Hanon | A61P 31/16 |
| 10,130,700 | B2 * | 11/2018 | Taubenberger | A61P 31/16 |

FOREIGN PATENT DOCUMENTS

| | | |
|---|---|---|
| CN | 101732711 | 6/2010 |

OTHER PUBLICATIONS

Anonymous, "Annex I, Summary of Product Characteristics," AFLUNOV suspension for injection in pre-filled syringe, https://www.ema.europa.eu/en/documents/product-information/aflunov-epar-product-information_en.pdf., Jan. 1, 2017, downloaded May 10, 2019, 30 pp.
Anonymous, "Package Leaflet: Information for the User," AGRIPPAL 2014/2015, Suspension for injection in pre-filled syringe, https://www.hpra.ie/img/uploaded/swedocuments/2154348.PA0919_001.edac2ec8-a54d-42aa-9a76-ae241135d10c.000001PIL.150304.pdf, Jan. 1, 2015, downloaded May 10, 2019, 8 pp.
Herbinger et al., "A Phase II Study of an Investigational Tetravalent Influenza Vaccine Formulation Combining MF59®," *Human Vaccin. Immunother.*, vol. 10:92-99, 2014.
International Search Report and Written Opinion from PCT/US2019/014220, dated May 23, 2019, 11 pages.
Schwartzman et al., "An Intranasal Virus-Like Particle Vaccine Broadly Protects Mice from Multiple Subtypes of Influenza A Virus," *mBio*, vol. 6:e010445-15, 2015.
Vemula et al., "Vaccine approaches conferring cross-protection against influenza viruses," *Expert Rev Vaccines*, vol. 16(11): 1141-1154, 2017.

* cited by examiner

*Primary Examiner* — Bao Q Li
(74) *Attorney, Agent, or Firm* — Klarquist Sparkman, LLP

(57) ABSTRACT

Universal influenza virus vaccine compositions that include multiple inactivated influenza A viruses are described. The compositions include four or more different influenza A viruses, each virus having a different hemagglutinin (HA) subtype. The vaccine compositions can be used, for example, to elicit an immune response against influenza virus, to immunize a subject against seasonal influenza virus, and/or mitigate a future pandemic by serving as a pre-pandemic vaccine.

32 Claims, 8 Drawing Sheets

Day 0 — Immunize Intranasally (6 μg)
Day 21 — Boost Intranasally (6 μg)
Day 50 — Challenge 10xLD$_{50}$ with various HA subtypes Vaccine = 1.5 μg total protein each of avian H1, H3, H5, H7 BPL-inactivated virus H6N1 Challenge, H7N1 Challenge, H10N1 Challenge, H10N7 Challenge Percent Survival · · · Vaccine IN (1)
— — Vaccine IM (2)
→ Mock (3)

Heterosubtypic protection

Heterosubtypic protection

H7N1 challenge

1 — IN - BPL H2/4/9/10
2 — IM - BPL H2/4/9/10
3 — Mock - BPL H2/4/9/10

100% survival

H15N1 challenge

1 — IN - BPL H2/4/9/10
2 — IM - BPL H2/4/9/10
3 — Mock - BPL H2/4/9/10

100% survival

BROADLY PROTECTIVE INACTIVATED INFLUENZA VIRUS VACCINE

CROSS REFERENCE TO RELATED APPLICATIONS

This application claims the benefit of U.S. Provisional Application No. 62/620,051, filed Jan. 22, 2018, which is herein incorporation by reference in its entirety.

FIELD

This disclosure concerns compositions that include a mixture of inactivated, low pathogenicity influenza virus strains, and their use to elicit broadly reactive immune responses against seasonal influenza and to inhibit zoonotic influenza pandemics.

BACKGROUND

Influenza virus is a member of the Orthomyxoviridae family There are three types of influenza viruses, designated influenza A, influenza B, and influenza C. Influenza A viruses infect not only humans but also many species of birds and mammals and are classified by the subtype of their surface proteins, hemagglutinin (HA) and neuraminidase (NA). The influenza A virion contains a segmented negative-sense RNA genome, which encodes the following proteins: hemagglutinin (HA), neuraminidase (NA), matrix (M1), proton ion-channel protein (M2), nucleoprotein (NP), polymerase basic protein 1 (PB1), PB1-F2, polymerase basic protein 2 (PB2), polymerase acidic protein (PA), PA-X, nonstructural protein 1 (NS1), and nonstructural protein 2 (NS2). The HA, NA, M1, and M2 proteins are membrane associated, whereas NP, PB1, PB2, PA, are nucleocapsid associated proteins, and the PB1-F2, NS2, and PA-X proteins are nonstructural proteins. The HA and NA proteins are envelope glycoproteins, with HA responsible for virus attachment and penetration of the viral particles into the cell and NA responsible for viral release, and are the sources of the major immunodominant epitopes for virus neutralization and protective immunity.

The public health burden of influenza is great, with an average of greater than 200,000 hospitalizations per year in the U.S., and resulting mortality of seasonal influenza ranging from 3,000 to 80,000 per year in the U.S. In pandemic years, these totals can increase dramatically. In 1918, during the worst influenza pandemic on record, 675,000 people died in the U.S. and up to 50-100 million people died globally. Additionally, novel strains of influenza with HA and NA subtypes for which most people do not have any immunity can emerge in animals (for example, birds and swine) and be transmitted to people. Zoonotically derived outbreaks can ensue which can lead to a pandemic. As an example, a swine H1N1 virus adapted to people to cause a pandemic in 2009. Bird-adapted strains of H5N1, H9N2, H7N9, H10N8 and H6N1 have all caused human infections, often with significant mortality.

Since the 2009 pandemic, zoonotic infections with H5N1, H7N9, H3N2 and recently H6N1 and H10N8 have been observed, stressing the need for a broadly reactive or universal vaccine approach that extends beyond protection against defined circulating seasonal variants, which could help prevent or mitigate a future pandemic by serving as a pre-pandemic vaccine. Live attenuated influenza vaccines are problematic because they are over-attenuated and have restricted usage guidelines. Furthermore, live viruses expressing hemagglutinin (HA) and/or neuraminidase (NA) subtypes not present in seasonal strains cannot be used because of the risk of reassortment with wild type viruses. Thus, there is a need for a broadly reactive vaccine that can generate a protective immune response without the requirement of employing a live attenuated virus. The major difficulty faced by universal influenza vaccine approaches is the antigenic variability of different HA and NA subtypes. A universal vaccine could serve as a pre-pandemic vaccine, providing protection against zoonotic influenza infections as well as providing protection against seasonal influenza virus strains, or both.

SUMMARY

Described herein are universal influenza virus vaccine compositions that include a mixture of low pathogenicity, inactivated influenza viruses. The compositions include four or more different influenza A viruses, each virus having a different hemagglutinin (HA) subtype and each virus being monovalent (e.g., each virus having only one HA subtype). The vaccine compositions can be used, for example, to elicit an immune response against influenza virus or to immunize a subject against seasonal influenza virus. The disclosed influenza virus compositions can also be used as a pre-pandemic vaccine to prevent or mitigate future zoonotic influenza pandemics.

Provided are compositions that include a first influenza A virus having a HA of a first subtype; a second influenza A virus having a HA of a second subtype; a third influenza A virus having a HA of a third subtype; and a fourth influenza A virus having a HA of a fourth subtype, wherein the four different influenza A viruses are inactivated. In some embodiments, the composition further includes a fifth, sixth, seventh and/or eight inactivated influenza A virus, each virus with a different HA subtype. In some examples, the first, second, third, fourth, fifth, sixth, seventh and/or eighth influenza viruses have an HA subtype selected from any one of H1, H2, H5, H6, H8, H9, H11, H12, H13 and H16. In some examples, the viruses are chemically inactivated. Each virus in the composition only has a single HA subtype (e.g., is monovalent).

Also provided are containers, such as syringes or vials, that include a composition disclosed herein. Kits that include a disclosed container are also provided.

Further provided are methods of eliciting an immune response to influenza virus in a subject by administering a therapeutically effective amount of a disclosed composition. Also provided are methods of immunizing a subject against influenza virus by administering a therapeutically effective amount of a disclosed composition. In some examples, the immune response obtained is heterosubtypic, that is, immune protection is achieved for an influenza subtype that is not in the composition administered to the subject (e.g., administer composition of influenza viruses separately bearing H1, H3, H5, and H7 HA subtypes (which may be chemically inactivated), and achieve an immune response or protection against an influenza H2, H4, H6 and/or H10) subtype).

The foregoing and other objects and features of the disclosure will become more apparent from the following detailed description, which proceeds with reference to the accompanying figures.

DETAILED DESCRIPTION

I. Abbreviations

Figure 1:
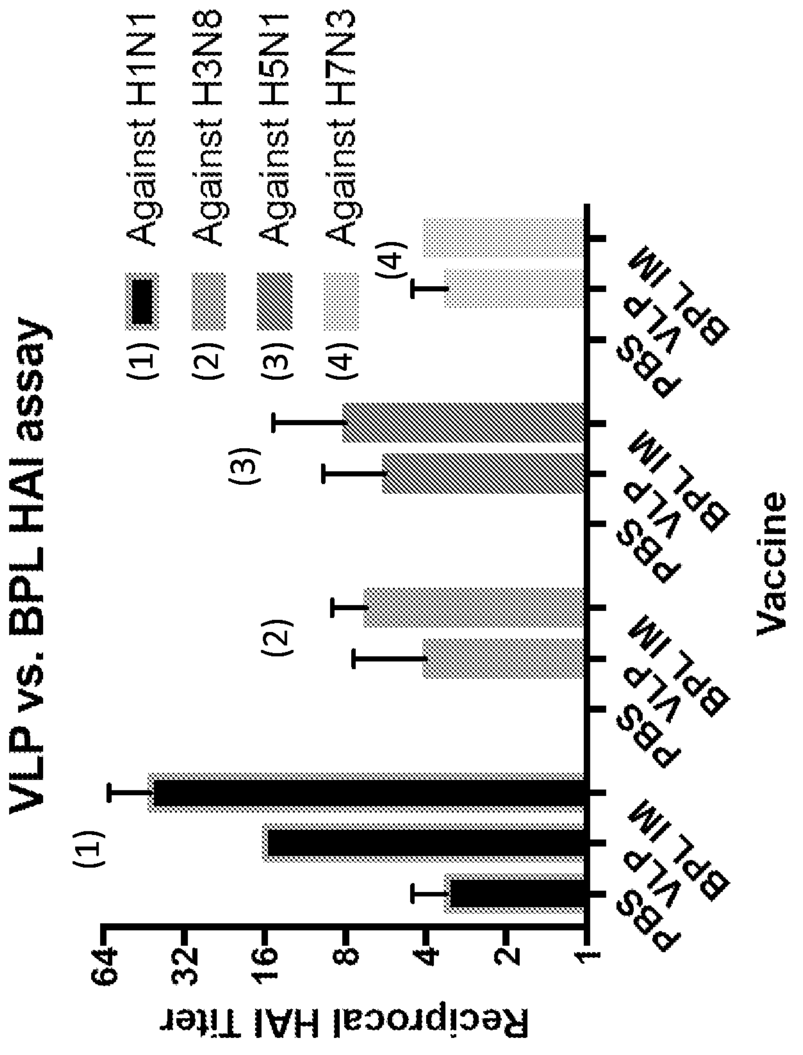
FIG. 1 is a graph showing reciprocal hemagglutination inhibition (HAI) titers of mice vaccinated with PBS (negative control), a tetravalent influenza virus-like particle (VLP) vaccine or a beta-propiolactone (BPL)-inactivated whole virus tetravalent influenza virus vaccine. Titers against H1N1, H3N8, H5N1 and H7N3 are shown. Both vaccines included HA from H1, H3, H5 and H7 influenza.

BPL beta-propiolactone
HA hemagglutinin
HAI hemagglutination inhibition
HAU hemagglutinating units
IAV influenza A virus
IBV influenza B virus
ICV influenza C virus
IM intramuscular
IN intranasal
NA neuraminidase
NI neuraminidase inhibiting
NP nucleoprotein
NS nonstructural
RBC red blood cell
RDE receptor destroying enzyme
RT room temperature
VLP virus-like particle
WHO World Health Organization

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen (for example, an influenza virus antigen). Adjuvants can be used with the compositions disclosed herein, for example a part of a pharmaceutical influenza virus vaccine composition provided herein. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL. In one example the adjuvant is one or more toll-like receptor (TLR) agonists, such as an agonist of TLR1/2 (which can be a synthetic ligand) (for example, Pam3Cys), TLR2 (for example, CFA, Pam2Cys), TLR3 (for example, polyLC, poly A:U), TLR4 (for example, MPLA, Lipid A, and LPS), TLR5 (for example, flagellin), TLR7 (for example, gardiquimod, imiquimod, loxoribine, Resiquimod®), TLR7/8 (for example, R0848), TLR8 (for example, imidazoquionolines, ssPolyU, 3M-012), TLR9 (for example, ODN 1826 (type B), ODN 2216 (type A), CpG oligonucleotides) and/or TLR11/12 (for example, profilin). In one example, the adjuvant is lipid A, such as lipid A monophosphoryl (MPL) from *Salmonella enterica* serotype Minnesota Re 595 (for example, Sigma Aldrich Catalog #L6895).

Administer: As used herein, administering a composition (such as one containing an influenza virus composition) to a subject means to give, apply or bring the composition into contact with the subject. Administration can be accomplished by any of a number of routes, such as, for example, intramuscular, intranasal, pulmonary, topical, oral, subcutaneous, intraperitoneal, intravenous, intrathecal, rectal, vaginal and intradermal.

Antibody: An immunoglobulin molecule produced by B lymphoid cells with a specific amino acid sequence. Antibodies are evoked in humans or other animals by a specific antigen (immunogen, such as influenza virus HA and NA). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen or immunogen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens.

Beta-propiolactone (BPL): An organic compound of the lactone family, with a four-membered ring. BPL is a chemical inactivating agent of infectious agents (including viruses) for vaccines. This chemical is an alkylating agent that reacts with many nucleophilic reagents, including nucleic acids and proteins. BPL treatment induces nicks in DNA and cross-linking between nucleic acid and proteins. BPL inhibits influenza virus fusion (Bonnafous et al., *Biochim Biophys Acta* 1838(1 Pt B):355-363, 2013). The chemical formula for BPL is $C_3H_4O_2$. BPL is also known as oxetan-2-one, 3-hydroxypropanoic acid lactone, propiolactone, β-propiolactone and 2-oxetanone.

Hemagglutinin (HA): An influenza virus surface glycoprotein. HA mediates binding of the virus particle to host cells and subsequent entry of the virus into the host cell. HA also causes red blood cells to agglutinate. HA (along with NA) is one of the two major influenza virus antigenic determinants.

Heterosubtypic immune response: An immune response elicited by infection or immunization with an influenza A virus that provides protection against infection by an influenza virus with another HA or NA subtype.

Immune response: A response of a cell of the immune system, such as a B-cell, T-cell, macrophage or polymorphonucleocyte, to a stimulus such as an antigen or vaccine (such as an influenza virus vaccine). An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). Methods of measuring immune responses include, for example, measuring proliferation and/or activity of lymphocytes (such as B or T cells), secretion of cytokines or chemokines, inflammation, antibody production and the like. Other examples are provided herein.

Immunize: To render a subject (such as a mammal) protected from an infectious disease (for example, influenza), such as by vaccination.

Inactivated: In the context of the present disclosure, an "inactivated" virus is one that has been altered to the extent that it not capable of establishing an infection in a host or host cell. Viruses can be inactivated using, for example, chemicals, heat, alterations in pH and/or irradiation (such as ultraviolet or gamma irradiation). Inactivated viruses are also referred to as "killed." A "chemically inactivated" virus is a virus that has been inactivated using a chemical method, such as treatment with BPL, formaldehyde, glutaraldehyde, 2,2'-dithiodipyridine or binary ethylene imine. For a review of inactivation methods for virus vaccines, see Delrue et al. (*Expert Rev Vaccines* 11(6):695-719, 2012).

Influenza virus: A segmented, negative-strand RNA virus that belongs to the Orthomyxoviridae family Influenza viruses are enveloped viruses. There are three types of influenza viruses, A, B and C.

Influenza A virus (IAV): A negative-sense, single-stranded, segmented RNA virus, which has eight RNA segments (PB2, PB1, PA, NP, M, NS, HA and NA) that code for 11 proteins, including RNA-directed RNA polymerase proteins (PB2, PB1 and PA), nucleoprotein (NP), neuraminidase (NA), hemagglutinin (subunits HA1 and HA2), the matrix proteins (M1 and M2) and the non-structural proteins (NS1 and NS2). This virus is prone to rapid evolution by error-protein polymerase and by segment reassortment. The host range of influenza A is quite diverse, and includes humans, birds (for example, chickens and aquatic birds), horses, marine mammals, pigs, bats, mice, ferrets, cats, tigers, leopards and dogs. Animals infected with influenza A often act as a reservoir for the influenza viruses and certain subtypes have been shown to cross the species barrier to humans Influenza A viruses can be classified into subtypes based on allelic variations in antigenic regions of two genes that encode surface glycoproteins, namely, hemagglutinin (HA) and neuraminidase (NA), which are required for viral attachment and cellular release. There are currently 18 different influenza A virus HA antigenic subtypes (H1 to H18) and 11 different influenza A virus NA antigenic subtypes (N1 to N11). 1-H16 and N1-N9 are found in wild bird hosts and may be a pandemic threat to humans. H17-H18 and N10-N11 have been described in bat hosts and are not currently thought to be a pandemic threat to humans.

Specific examples of influenza A include, but are not limited to: H1N1 (such as 1918 H1N1), H1N2, H1N7, H2N2 (such as 1957 H2N2), H2N1, H3N1, H3N2, H3N8, H4N8, H5N1, H5N2, H5N8, H5N9, H6N1, H6N2, H6N5, H7N1, H7N2, H7N3, H7N4, H7N7, H7N9, H8N4, H9N2, H10N1, H10N7, H10N8, H11N1, H11N6, H12N5, H13N6, and H14N5. In one example, influenza A includes those known to circulate in humans such as H1N1, H1N2, H3N2, H7N9, and H5N1.

In animals, most influenza A viruses cause self-limited localized infections of the respiratory tract in mammals and/or the intestinal tract in birds. However, highly pathogenic influenza A strains, such as H5N1, cause systemic infections in poultry in which mortality may reach 100%. In 2009, H1N1 influenza was the most common cause of human influenza. A new strain of swine-origin H1N1 emerged in 2009 and was declared pandemic by the World Health Organization. This strain was referred to as "swine flu." H1N1 influenza A viruses were also responsible for the Spanish flu pandemic in 1918, the Fort Dix outbreak in 1976, and the Russian flu epidemic in 1977-1978.

Influenza B virus (IBV): A negative-sense, single-stranded, RNA virus, which has eight RNA segments. IBV has eight RNA segments (PB1, PB2, PA, HA, NP, NA, M1 and NS1) that code for 11 proteins, including RNA-directed RNA polymerase proteins (PB1, PB2 and PA), nucleoprotein (NP), neuraminidase (NA), hemagglutinin (subunits HA1 and HA2), matrix protein (M1), non-structural proteins (NS1 and NS2) and ion channel proteins (NB and BM2). This virus is less prone to evolution than influenza A, but it mutates enough such that lasting immunity has not been achieved. The host range of influenza B is narrower than influenza A, and is only known to infect humans and seals. Influenza B viruses are not divided into subtypes, but can be further broken down into lineages and strains. Specific examples of influenza B include, but are not limited to: B/Yamagata, B/Victoria, B/Shanghai/361/2002 and B/Hong Kong/330/2001.

Influenza C virus (ICV): A negative-sense, single-stranded, RNA virus, which has seven RNA segments that encode nine proteins. ICV is a genus in the virus family Orthomyxoviridae. ICV infects humans and pigs and generally causes only minor symptoms, but can be severe and cause local epidemics. Unlike IAV and IBV, ICV does not have the HA and NA proteins. Instead, ICV expresses a single glycoprotein called hemagglutinin-esterase fusion (HEF).

Isolated: An "isolated" biological component (such as a nucleic acid, protein, or virus) has been substantially separated or purified away from other biological components (such as cell debris, or other proteins or nucleic acids). Biological components that have been "isolated" include those components purified by standard purification methods. The term also embraces recombinant nucleic acids, proteins, viruses, as well as chemically synthesized nucleic acids or peptides.

Neuraminidase (NA): An influenza virus membrane glycoprotein. NA is involved in the destruction of the cellular receptor for the viral HA by cleaving terminal sialic acid residues from carbohydrate moieties on the surfaces of infected cells. NA also cleaves sialic acid residues from viral proteins, preventing aggregation of viruses. NA (along with HA) is one of the two major influenza virus antigenic determinants Outbreak: As used herein, an influenza virus "outbreak" refers to a collection of virus isolates from within a single country or region in a given year.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compositions, such as one or more influenza virus compositions disclosed herein, and additional pharmaceutical agents.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Purified: The term "purified" does not require absolute purity; rather, it is intended as a relative term. Thus, for example, a purified protein, virus, nucleic acid or other compound is one that is isolated in whole or in part from naturally associated proteins and other contaminants. In certain embodiments, the term "substantially purified" refers to a protein, virus, nucleic acid or other active compound that has been isolated from a cell, cell culture medium, or other crude preparation and subjected to fractionation to remove various components of the initial preparation, such as proteins, cellular debris, and other components.

Subject: Living multi-cellular vertebrate organisms, a category that includes both human and non-human mammals, such as non-human primates. In one example a subject is one that can be infected with influenza virus, such as humans, birds (for example, chickens, turkeys), horses, pigs, bats, mice, ferrets, cats, tigers, leopards, seals and dogs. As used herein, a "pediatric subject" is a human subject under the age of 21; an "adult subject" is a human subject 21 years or older.

Therapeutically effective amount: A quantity of a specified agent sufficient to achieve a desired effect in a subject being treated with that agent. For example, this may be the amount of an influenza virus composition useful for eliciting an immune response in a subject and/or for preventing infection or disease caused by influenza virus. In one example, a therapeutically effective amount of an influenza virus composition is an amount sufficient to increase resistance to, prevent, ameliorate, and/or treat infection caused by influenza virus (such as influenza A, influenza B, or both) in a subject without causing a substantial cytotoxic effect in the subject. The effective amount of an influenza virus composition useful for increasing resistance to, preventing, ameliorating, and/or treating infection in a subject will be dependent on, for example, the subject being treated, the manner of administration of the therapeutic composition and other factors.

Vaccine: A preparation of immunogenic material capable of stimulating an immune response, administered for the prevention, amelioration, or treatment of disease, such as an infectious disease. The immunogenic material may include an influenza virus composition disclosed herein. Vaccines may elicit both prophylactic (preventative) and therapeutic responses. Methods of administration vary according to the vaccine, but can include inoculation, ingestion, intranasal, intramuscular or other forms of administration. Vaccines may be administered with an adjuvant to enhance the immune response.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Influenza A virus infections are a major global public health problem. According to the World Health Organization (WHO), annual epidemics result in approximately 3-5 million severe illnesses and up to 500,000 deaths. Zoonotic outbreaks, in which people are infected with animal-derived influenza viruses like avian influenza H5N1 or H7N9 strains, can result in extremely high case fatality rates and also pose a significant risk for the development of new pandemic influenza strains. Influenza pandemics vary in their impact, but the 1918 influenza pandemic resulted in at least 50 million deaths globally, and was likely derived from an avian influenza virus. The pandemics of 1957 and 1968 also had avian influenza derived surface protein genes. Unlike some infectious diseases, influenza cannot be eradicated, because the causative influenza A viruses are maintained through silent infections of the gastrointestinal tract of wild birds. These avian viruses form 144 possible subtypes, based on the expression of a combination of one of 16 subtypes of the surface hemagglutinin (HA) molecule with one of 9 neuraminidase (NA) subtypes. The emergence in humans of a host-adapted zoonotically derived influenza A virus with a novel HA (and/or NA), to which humans lack immunity, is the cause of pandemics. The current public health strategy for preventing influenza is based on the development of a new vaccine each year against specific circulating virus strains. This approach is inadequate, in part because the annual production and mass delivery of new vaccines is enormously expensive, but principally because these annual vaccines only target circulating viruses, so that they cannot prevent the emergence of a new pandemic virus with a novel HA subtype.

To address this problem, the present disclosure describes a multivalent vaccine for immunizing animals simultaneously against all influenza A virus subtypes maintained in wild birds. PCT Publication WO 2015/195218 describes a study in which a mixture of non-infectious virus-like particles (VLPs) expressing 4 different low pathogenicity (low path) avian HAs (H1, H3, H5, H7) were delivered intranasally to laboratory animals, and the mixture induced broadly reactive immunity to a wide variety of influenza A virus subtypes (including the 1918 H1N1 virus, high path avian H5N1 and avian H7N9 viruses). The VLP mixture also provided cross-protection against viruses with HA subtypes not represented in the vaccine (1957 H2N2 virus, and avian H6, H10, H11, and H15 viruses). Vaccination with the VLP mixture did not provide sterilizing immunity following intersubtypic 10× lethal dose challenge; however, the vaccine cocktail did prevent serious illness and protected animals from death.

The present disclosure describes vaccination with a beta-propiolactone (BPL) inactivated whole virus vaccine consisting of multiple (such as 4, 6 or 8) different low pathogenicity avian subtypes. The BPL-inactivated influenza virus cocktail, when administered intranasally or intramuscularly, provided extremely broad protection and heterosubtypic protection to lethal challenge, for example as compared to a VLP mixture with the same HAs.

VLP manufacture is currently expensive, while a whole virus inactivated vaccine is more economical to manufacture and would not require development of new manufacturing methods. Further, because the vaccine consists of inactivated whole viruses, such a vaccine would not be susceptible to reassortment like live-attenuated vaccines. The inactivated whole virus vaccines can also promote the development of antibody responses to the HA head and stalk regions, NA and M2e surface proteins, as well as T-cell epitopes against other viral proteins in the inactivated virus vaccine.

IV. Overview of Embodiments

Universal influenza virus vaccine compositions that include multiple inactivated influenza A viruses are described. The compositions include four or more different influenza A viruses (such as 4, 5, 6, 7, 8, 9, 10, 11, 12, 13, 14, 15, or 16 different influenza A viruses), each virus having a different HA subtype, and wherein each virus is monovalent (e.g., has only a single HA subtype, such as only H1 or only H5, but not both H1 and H5). The compositions can be used, for example, to elicit an immune response against influenza virus, to immunize a subject against seasonal influenza virus and/or mitigate a future pandemic by serving as a pre-pandemic vaccine. In some examples, the compositions elicit an immune response against influenza virus subtype that is not in the composition, that is, provide a heterosubtypic immune response. For example, if the composition includes influenza viruses with subtypes H1, H3, H5 and H7, a heterosubtypic immune response could be against influenza virus H2, H4, H6, H8, H9, H10, H11, H12, H13, H14, H15 and/or H16. Similarly, if the composition includes influenza viruses with subtypes H2, H4, H9 and H10, a heterosubtypic immune response could be against influenza virus H1, H3, H5, H6, H7, H8, H11, H12, H13, H14, H15 and/or H16.

Disclosed are compositions that include a first influenza A virus comprising a HA of a first subtype, a second influenza A virus comprising a HA of a second subtype, a third influenza A virus comprising a HA of a third subtype, and a fourth influenza A virus comprising a HA of a fourth subtype, wherein the at least four different influenza A viruses are inactivated.

In some embodiments, at least one influenza A virus is a low pathogenicity avian influenza virus. In particular examples, at least two, at least three or all four influenza A viruses are low pathogenicity avian influenza viruses.

In some embodiments, at least one of the first, second, third and fourth HA subtypes are selected from H3, H4, H7, H10, H14 and H15. In some examples, at least two of the first, second, third and fourth HA subtypes are selected from H3, H4, H7, H10, H14 and H15.

In some embodiments, at least one of the first, second, third and fourth HA subtypes are selected from H1, H2, H5, H6, H8, H9, H11, H12, H13 and H16. In some examples, at least two of the first, second, third and fourth HA subtypes are selected from H1, H2, H5, H6, H8, H9, H11, H12, H13 and H16.

In some embodiments, at least one of the first, second, third and fourth HA subtypes are selected from H3, H4, H7, H10, H14 and H15; and at least one of the first, second, third and fourth HA subtypes are selected from H1, H2, H5, H6, H8, H9, H11, H12, H13 and H16. In some examples, at least two of the first, second, third and fourth HA subtypes are selected from H3, H4, H7, H10, H14 and H15; and at least two of the first, second, third and fourth HA subtypes are selected from H1, H2, H5, H6, H8, H9, H11, H12, H13 and H16.

Figure 3:
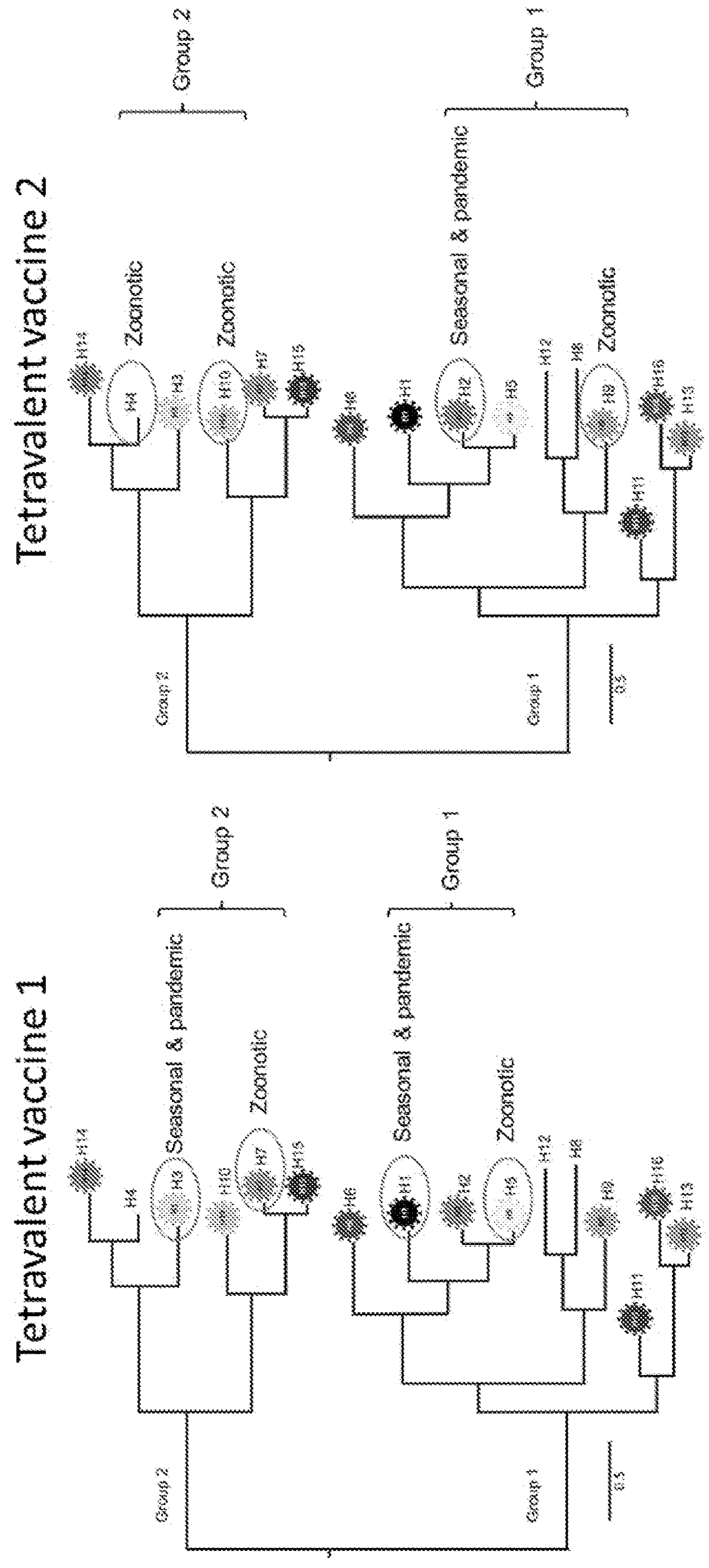
FIG. 3 includes two dendrograms of hemagglutinin (HA) subtypes showing the composition of tetravalent vaccine 1 (containing HA subtypes H1, H3, H5 and H7), and tetravalent vaccine 2 (containing HA subtypes H2, H4, H9 and H10).

In some examples, the first, second, third and fourth HA subtypes are H1, H3, H5 and H7, respectively (see FIG. 3, tetravalent vaccine 1). In specific non-limiting examples, the H1 virus is A/mallard/Ohio/265/1987 (H1N9), the H3 virus A/pintail/Ohio/339/1987 (H3N8), the H5 virus is A/mallard/Maryland/802/2007 (H5N1), and/or the H7 virus is A/Environment/Maryland/261/2006 (H7N3). In other examples, the first, second, third and fourth HA subtypes are H2, H4, H9 and H10 (see FIG. 3, tetravalent vaccine 2). In specific non-limiting examples, the H2 virus is A/green-winged teal/Ohio/175/1986 (H2N1), the H4 virus is A/green-winged teal/Ohio/344/1986 (H4N2), the H9 virus is A/Mallard/Maryland/798/2007 (H9N1) and/or the H10 virus is A/Mallard/Ohio/99/1989 (H10N7).

In some embodiments, the composition further includes a fifth influenza A virus comprising a HA of a fifth subtype, wherein the fifth influenza A virus is inactivated. In some examples, the composition further includes a sixth influenza A virus comprising a HA of a sixth subtype, wherein the sixth influenza A virus is inactivated. In some examples, the composition further includes a seventh influenza A virus comprising a HA of a seventh subtype, wherein the seventh influenza A virus is inactivated. In some examples, the composition further includes an eighth influenza A virus comprising a HA of an eighth subtype, wherein the eighth influenza A virus is inactivated.

Phylogenetically, there are two major groups of influenza A virus HAs: group 1 contains H1, H2, H5, H6, H8, H9, H11, H12, H13, and H16, and group 2 contains H3, H4, H7, H10, H14, and H15 subtypes (see FIG. 3). In some embodiments of the compositions disclosed herein, the composition includes at least one influenza A virus with a group 1 HA and at least one influenza A virus with a group 2 HA. In particular examples, half of the viruses in the composition (such as 2, 3 or 4 viruses) have a group 1 HA and half of the viruses (such as 2, 3 or 4 viruses) have a group 2 HA.

In some embodiments, the first, second, third, fourth fifth, sixth, seventh and/or eighth HA subtypes are H1, H2, H3, H4, H5, H7, H9 and H10 (for example, a combination of tetravalent vaccines 1 and 2 in FIG. 3). In specific non-limiting examples, the H1 virus is A/mallard/Ohio/265/1987 (H1N9), the H3 virus A/pintail/Ohio/339/1987 (H3N8), the H5 virus is A/mallard/Maryland/802/2007 (H5N1), the H7 virus is A/Environment/Maryland/261/2006 (H7N3), the H2 virus is A/green-winged teal/Ohio/175/1986 (H2N1), the H4 virus is A/green-winged teal/Ohio/344/1986 (H4N2), the H9 virus is A/Mallard/Maryland/798/2007 (H9N1) and/or the H10 virus is A/Mallard/Ohio/99/1989 (H10N7).

The influenza A viruses of the disclosed compositions are inactivated. The viruses can be inactivated using any means known in the art. In some embodiments, the influenza A viruses are chemically inactivated. In some examples, the influenza A viruses are chemically inactivated with beta-propiolactone (BPL). In other examples, the influenza A viruses are chemically inactivated with formaldehyde. In other examples, the influenza A viruses are chemically inactivated with glutaraldehyde, 2,2'-dithiodipyridine or binary ethylene imine. In other embodiments, the influenza A viruses are inactivated with heat. In yet other embodiments, the influenza A viruses are inactivated with irradiation. In some examples, the influenza A viruses are inactivated with ultraviolet or gamma irradiation.

In some embodiments, the composition further includes a pharmaceutically acceptable carrier, an adjuvant, or both.

In some embodiments, the composition is formulated for intranasal administration. In other embodiments, the composition is formulated for intramuscular administration.

Also provided are containers that include a composition disclosed herein. In some embodiments, the container is a syringe. In some examples, the syringe includes a needle. The plunger in a syringe can have a stopper to prevent the plunger from being accidentally removed during aspiration. Disposable syringes generally contain a single dose of vaccine. The syringe can have a tip cap to seal the tip prior to attachment of a needle. In non-limiting examples, the tip cap is made of rubber, such as a butyl rubber.

In other embodiments, the container is a vial. In some examples, the vial is made of glass, such as a colorless glass, for example borosilicate. In other examples, the vial is made of plastic. The vial can include a stopper, such as a rubber stopper, or a cap, such as cap adapted to enable insertion of a syringe. In some examples, the vial includes a single dose of the composition. In other examples, the vial includes multiples doses of the composition, such as 2, 3, 4, 5, 6, 7, 8, 9 or 10 or more doses of the composition. Generally, the vial is sterilized prior to adding the composition.

Also provided are kits that include a container disclosed herein. In some embodiments, the kits includes a vial (such as a vial containing the composition), a syringe (for example, an empty syringe or a syringe containing the composition), a needle, or any combination thereof. The compositions can be in a suspension, such as in PBS or other pharmaceutically acceptable carrier. Alternatively, the compositions can be in a dried or powered form, such as lyophilized or freeze dried, which can then be reconstituted by an end user (for example with PBS or other pharmaceutically acceptable carrier). The containers in the kit can include an adjuvant, or the adjuvant can be in a separate container in the kit. In some examples the containers can include a pharmaceutically acceptable carrier, such as PBS, or the pharmaceutically acceptable carrier, such as PBS, can be in a separate container (for example if the compositions are freeze-dried or lyophilized). In some examples, the containers in the kit further include one or more stabilizers. In some examples, the kits also include a device that permits administration of the composition to a subject. Examples of such devices include a syringe or syringe atomizer (for example an MAD® nasal drug delivery device, such as those from Life Medicals Supplier, Sunrise, Fla.). A kit can be packaged (for example, in the same box) with a leaflet including details of the vaccine, such as instructions for administration and/or details of the viruses within the vaccine.

Further provided are methods of eliciting an immune response to influenza virus in a subject by administering a therapeutically effective amount of a composition disclosed herein to a subject. Also provided are methods of immunizing a subject against influenza virus by administering to the subject a therapeutically effective amount of a composition disclosed herein. In some embodiments, the composition is administered intramuscularly. In other embodiments, the composition is administered intranasally. In some embodiments, the subject is a mammal or a bird. In other embodiments, the subject is a human.

The compositions disclosed herein can be used for treatment (such as vaccination) of both children and adults. Influenza vaccines are currently recommended for use in both pediatric and adult subjects, from the age of 6 months. Thus, in some embodiments, the human is an adult subject. In other embodiments, the human is a pediatric subject. Accordingly, the human subject may be less than 1 year old (such as at least six months, at least seven months, at least eight months, at least 9 months, at least 10 months, or at least 11 months old), 1-5 years old (such as at least 1 year, at least 2 years, at least 3 year or at least 4 years old), 5-15 years old, 15-21 years old, 21-55 years old, 55-65 years old, or at least 65 years old. In particular non-limiting examples, the patient is an elderly patient, such as a patient at least 65 years old. In some examples, the subject is a hospitalized patient, a healthcare worker, an armed service member, military personnel, a pregnant woman, a chronically ill patient, an immunodeficient patient, a patient who has previously taken an antiviral compound, a person with an egg allergy or a person travelling abroad.

V. Compositions

Provided herein are compositions that contain at least four (such as at least five, at least six, at least seven or at least eight) different low pathogenicity avian influenza viruses. Each virus in the composition contains a different subtype of HA. In some embodiments, half of the viruses (such as 2, 3 or 4 of the viruses) have a group 1 HA subtype (H1, H2, H5, H6, H8, H9, H11, H12, H13 and H16) and half of the viruses (such as 2, 3 or 4 of the viruses) have a group 2 HA subtype (H3, H4, H7, H10, H14 and H15). All of the viruses in the composition are inactivated, such as chemically inactivated, for example chemically inactivated with BPL. Representative (non-limiting) influenza virus strains having subtype H1-H16 that can be used in the disclosed compositions are shown in Table 1.

TABLE 1

| Source of HA Genes for production of inactivated influenza virus vaccine cocktails | | |
|---|---|---|
| HA Subtype | Influenza A Virus HA Donor Strain | GenBank ™ Accession No. |
| H1 | A/mallard/Ohio/265/1987 (H1N9) | CY017275.1 |
| H2 | A/green-winged teal/Ohio/175/1986 (H2N1) | CY018877.1 |
| H3 | A/pintail/Ohio/339/1987 (H3N8) | CY019197.1 |
| H4 | A/green-winged teal/Ohio/344/1986 (H4N2) | CY015459.1 |
| H5 | A/mallard/Maryland/802/2007 (H5N1) | CY017781.1 |
| H6 | A/Mallard/Ohio/249/1998 (H6N1) | CY015476.1 |
| H7 | A/Environment/Maryland/261/2006 (H7N3) | CY022749.1 |
| H8 | A/Mallard/Alaska/708/2005 (H8N4) | CY017749.1 |
| H9 | A/Mallard/Maryland/798/2007 (H9N1) | CY053877.1 |
| H10 | A/Mallard/Ohio/99/1989 (H10N7) | CY017781.1 |
| H11 | A/green-winged teal/Ohio/340/1987 (H11N9) | CY021869.1 |
| H12 | A/Mallard/Minnesota/-Sg-00055/2007 (H12N5) | CY033700.1 |
| H13 | A/Gull/MD/16/1985 (H13N2) | KP033522 |
| H14 | A/mallard duck/Astrakhan/263/1982 (H14N5) | CY130094.1 |
| H15 | A/Australian Shelduck-Western/1756/1983 (H15N2) | CY006032.1 |
| H16 | A/Glaucous gull/Alaska/44198-027/2006 (H16N3) | HM059998.1 |

Other exemplary (non-limiting) strains having any of H1-H16 that can be used in the disclosed compositions are shown in Table 2.

TABLE 2

| Exemplary Influenza Viruses | | |
|---|---|---|
| Subtype | Influenza A Virus Strains | GenBank ™ Accession No. |
| H1 | A/South Carolina/1/1918(H1N1) | AAD17229.1 |
| H2 | A/Japan/305/1957(H2N2) | AAA43185.1 |
| H3 | A/turkey/England/1969(H3N2) | AAT08004.1 |
| | A/duck/Chiba/15/2008(H3N8) | BAJ09300.1 |
| H4 | A/ruddy turnstone/New Jersey/47/1985(H4N6) | AAA43222.1 |
| | A/gray teal/Australia/2/1979(H4N4) | AAA43217.1 |
| | A/duck/Czechoslovakia/1956(H4N6) | AAA43216.1 |
| H5 | A/Duck/Hong Kong/380.5/2001(H5N1) | AAL75847.1 |
| | A/Chicken/Hong Kong/317.5/2001(H5N1) | AAL75839.1 |
| H6 | A/chicken/California/6643/2001(H6N2) | AAO33485.1 |
| | A/chicken/California/431/2000(H6N2) | AAO33479.1 |
| H7 | A/chicken/Italy/1067/1999(H7N1) | CAE48276.1 |
| | A/swan/Czech Republic/5416/2011(H7N7) | AET50899.1 |
| H8 | A/northern shoveler/Mississippi/11OS5900/2011(H8N1) | AHL82381.1 |
| H9 | A/Chicken/Korea/MS96/96(H9N2) | AAF69255.1 |
| | A/chicken/England/1415-51184/2010(H9N1) | AFC18325.1 |
| | A/turkey/Netherlands/11015452/2011(H9N2) | AFO83303.1 |
| H10 | A/fowl/Hampshire/PD378/1985(H10N4) | ACS89022.1 |
| | A/mallard/Gloucestershire/PD374/1985(H10N4) | ACS89011.1 |
| | A/chicken/Germany/N/1949(H10N7) | ACS89000.1 |
| H11 | A/chicken/New Jersey/4236-18/1993(H11N3) | ABD66294.1 |
| | A/chicken/New Jersey/15906-9/1996(H11N1) | ABD91532.1 |
| | A/guinea fowl/New Jersey/8848-17/1998(H11N2) | ABD66297.1 |
| H12 | A/mallard/Maryland/1153/2005(H12N5) | ABO52621.1 |
| | A/northern pintail/Alaska/44160-060/2006(H12N5) | ACE73380.1 |
| H13 | A/Larus argentatus/Astrakhan/458/1985(H13N6) | ACA48473.1 |
| | A/great black-headed gull/Astrakhan/1421/79(H13N2) | ACA48470.1 |
| | A/great black-headed gull/Astrakhan/1420/79(H13N2) | ACA48469.1 |

TABLE 2-continued

| Exemplary Influenza Viruses | | |
|---|---|---|
| Subtype | Influenza A Virus Strains | GenBank ™ Accession No. |
| H14 | A/long-tailed duck/Wisconsin/10OS4225/2010(H14N6) | AEP68849.2 |
| | A/long-tailed duck/Wisconsin/10OS3912/2010(H14N6) | AEP68847.2 |
| | A/blue-winged teal/Guatemala/CIP049H106-62/2011(H14N6) | AHJ57322.1 |
| H15 | A/duck/Australia/341/1983(H15N8) | AAA92247.1 |
| | A/shearwater/West Australia/2576/79(H15N9)) | AAA96134.1 |
| H16 | A/black-headed gull/Turkmenistan/13/76(H16N3) | ACA48475.1 |
| | A/California gull/California/1196P/2013(H16N3) | AHM98288.1 |
| | A/environment/California/1242V/2012(H16N3) | AHM97554.1 |

A. Exemplary Components of the Composition

The inactivated influenza virus-containing compositions provided herein can include other agents. In some examples, the inactivated influenza viruses are present in a pharmaceutically acceptable carrier such as saline, buffered saline, dextrose, water, glycerol, sesame oil, ethanol, and combinations thereof. The carrier and composition can be sterile. The composition can also contain minor amounts of wetting or emulsifying agents, or pH buffering agents. The composition can also contain conventional pharmaceutical adjunct materials such as, for example, pharmaceutically acceptable salts to adjust the osmotic pressure, buffers, preservatives and the like. The composition can be a liquid solution, suspension, emulsion, tablet, pill, capsule, sustained release formulation, or powder. In one example, the composition is a liquid, or a lyophilized or freeze-dried powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate.

In some examples, the inactivated influenza virus-containing compositions include a pharmaceutically acceptable carrier and an adjuvant, such as a mucosal adjuvant, for example as one or more of CpG oligodeoxynucleotides, Flt3 ligand, and monophosphoryl lipid A (MLA). In one example, the adjuvant includes MLA, such as a clinical grade formulation, for example MPL® (3-O-desacyl-4'-monophosphoryl lipid A) adjuvant.

B. Formulations for Mucosal Administration

The inactivated influenza virus-containing compositions provided herein can be formulated for mucosal vaccination, such as intranasal administration. Mucosal vaccination can be achieved by a number of routes including oral, intranasal, pulmonary, rectal and vaginal. In a specific example, this is achieved by intranasal administration. Thus, in some examples the disclosed compositions are formulated for intranasal administration.

For example, the disclosed compositions can include one or more biodegradable, mucoadhesive polymeric carriers. Polymers such as polylactide-co-glycolide (PLGA), chitosan, alginate and carbopol can be included. Hydrophilic polymers, like sodium alginate and carbopol, absorb to the mucus by forming hydrogen bonds, consequently enhancing nasal residence time, and thus can be included in the disclosed compositions.

In one example, the composition includes sodium alginate, which is a linear copolymer and consists of 1-4-linked β-d-mannuronic acid and 1-4-linked α-1-guluronic acid residues. In some examples, the composition includes alginate microspheres. In one example, the composition includes carbopol (a cross-linked polyacrylic acid polymer), for example in combination with starch. In some examples, the composition includes chitosan, a non-toxic linear polysaccharide that can be produced by chitin deacetylation. In one example the chitosan is in the form of chitosan nanoparticles, such as N-trimethyl chitosan (TMC)-based nanoparticles.

In one example, the composition is formulated as a particulate delivery system used for nasal administration. In one example the inactivated influenza virus-containing composition can include liposomes, immune-stimulating complexes (ISCOMs) and/or polymeric particles, such as virosomes. In one example, the liposome is surface-modified (for example, glycol chitosan or oligomannose coated). In one example, the liposome is fusogenic or cationic-fusogenic.

The inactivated influenza virus-containing compositions can also include one or more lipopeptides of bacterial origin, or their synthetic derivatives. Examples of lipid moieties include tri-palmitoyl-S-glyceryl cysteine (Pam3Cys), di-palmitoyl-S-glyceryl cysteine (Pam2Cys), single/multiple-chain palmitic acids and lipoamino acids (LAAs).

The inactivated influenza virus-containing compositions can also include one or more adjuvants, for example a mucosal adjuvant, such as one or more of CpG oligodeoxynucleotides (CpG ODN), Flt3 ligand, and monophosphoryl lipid A (MLA). In one example, the adjuvant includes a clinical grade MLA formulation, such as MPL® (3-O-desacyl-4'-monophosphoryl lipid A) adjuvant.

V. Methods of Stimulating an Immune Response

Methods of using the disclosed inactivated influenza virus-containing compositions are provided herein. In one example, the methods include eliciting a broadly reactive immune response to influenza virus (such as influenza A, influenza B, or both) in a subject. In another example, the methods include immunizing or vaccinating a subject against influenza virus (such as influenza A, influenza B, or both) in a subject.

For example, the disclosed inactivated influenza viruses can stimulate a broadly-reactive immune response such that the subject administered the inactivated influenza virus composition is protected from serious illness or death from a wide variety of influenza A viruses (and/or influenza B viruses) without the need for a match between the challenge strain and the composition of the vaccine. It is shown herein that broad cross protection was achieved where the inactivated influenza virus composition did not contain the same HA subtype as the challenge strain (for example, challenge strain as H6N1, H10N1 or H10N7, but the composition did not include any viruses of subtype H6 or H10) (i.e., heterosubtypic protection). Thus, the disclosed inactivated influenza virus compositions can be used as a pre-pandemic vaccine.

Thus, in some examples, the immune response elicited using the disclosed compositions is to one or more of (such as at least 2, at least 3, at least 4, or at least 5 of) H1N1, H1N2, H1N7, H2N1, H2N2, H3N1, H3N2, H3N8, H4N8, H5N1, H5N2, H5N8, H5N9, H6N1, H6N2, H6N5, H7N1, H7N2, H7N3, H7N4, H7N7, H7N9, H8N4, H9N2, H10N1, H10N7, H10N8, H11N1, H11N6, H12N5, H13N6 and H14N5. In some examples, the immune response is to one or more of H1N1, H1N2, H3N2, H7N9 and H5N1. In some examples, such immunization provides protection (for example, prevents infection or prevents the development of disease associated with infection) against challenge by one or more of (such as at least 2, at least 3, at least 4, or at least 5 of) H1N1, H1N2, H1N7, H2N1, H2N2, H3N1, H3N2, H3N8, H4N8, H5N1, H5N2, H5N8, H5N9, H6N1, H6N2, H6N5, H7N1, H7N2, H7N3, H7N4, H7N7, H7N9, H8N4, H9N2, H10N1, H10N7, H10N8, H11N1, H11N6, H12N5, H13N6 and H14N5. In some examples, such immunization provides protection (for example, prevents infection or prevents the development of disease associated with infection) against challenge by one or more of H1N1, H1N2, H3N2, H7N9 and H5N1. In one example, the inactivated influenza virus compositions disclosed herein can be used as influenza vaccines to elicit a protective immune response against H1N1 and/or H3N2 influenza viruses.

In some examples, the immune response or immunization is with a mixture of inactivated influenza viruses expressing different HA subtypes than for which at least one immune response or protection is achieved. For example, if the subject is administered with a mixture of inactivated virus expressing H2, H3, H5 and H7, at least one of the immune responses or immunization can be achieved with an H1 influenza virus, such as H1N1. For example, if the subject is administered with a mixture of inactivated virus expressing H1, H3, H5 and H7, at least one of the immune responses or immunization can be achieved with one or more of an H2, H4, H6, H8, H9, H10, H11, H12, H13, H14, H15, and H16 influenza virus.

In some embodiments, the disclosed inactivated influenza virus-containing composition is administered using any suitable route of administration, such as, intranasal or intramuscular. In some embodiments, the inactivated influenza virus-containing composition includes a pharmaceutically acceptable carrier and/or an adjuvant. For example, the pharmaceutically acceptable carrier can be saline, such as sterile PBS pH 7.2-pH 7.4. For example, the adjuvant can be one or more of immunostimulatory oligonucleotides (such as CpG oligonucleotides), Flt3 ligand, and monophosphoryl lipid A (MLA).

The disclosed compositions can be used to stimulate or elicit an immune response to influenza virus (such as influenza A, B or both) in a subject. In some examples the method includes administering a therapeutically effective amount of a composition containing the inactivated influenza viruses provided herein to a subject, thereby eliciting an immune response to influenza virus in a subject. Methods of determining whether an immune response has been stimulated or elicited are known, and some examples are provided herein. In some examples, a positive immune response or immunization is achieved if there is an observed reduction in illness (such as less weight loss, reduction in symptoms, or reduction in lung pathology), reduction in viral titers, and/or protection from death. Thus, in some examples, the disclosed methods and/or compositions reduce weight loss by at least 10%, at least 20%, at least 30%, at least 40%, or at least 50% (for example within 6 to 15 days post challenge), for example as compared to an equivalent subject not receiving the influenza virus composition. In some examples, the disclosed methods and/or compositions reduce symptoms of influenza infection by at least 10%, at least 20%, at least 30%, at least 40%, or at least 50%, for example as compared to an equivalent subject not receiving the composition. In some examples, the disclosed methods and/or compositions reduce lung pathology due to influenza infection by at least 10%, at least 20%, at least 30%, at least 40%, or at least 50%, for example as compared to an equivalent subject not receiving the composition. In some examples, the disclosed methods and/or compositions reduce lung viral titer by at least 50%, at least 100%, at least 2-fold, at least 3-fold, at least 4-fold, or at least 5-fold, for example as compared to an equivalent subject not receiving the composition. In some examples, the disclosed methods and/or compositions increase survival following subsequent viral challenge by at least 10%, at least 20%, at least 30%, at least 40%, at least 50%, at least 75%, at least 80%, at least 90%, or at least 94%, for example as compared to an equivalent subject not receiving the composition. In some examples, the immune response achieved using the disclosed compositions is better than the immune response achieved using equivalent VLPs. Thus, in some examples, the disclosed compositions have an improved ability to stimulate or elicit an immune response as compared to equivalent VLPs.

The disclosed compositions can be used to immunize or vaccinate a subject against influenza virus, such as a mammalian subject or an avian subject. In some examples the method includes administering a therapeutically effective amount of a composition containing the inactivated influenza viruses provided herein to a subject, thereby immunizing the subject against influenza virus. In some examples, a positive immune response or immunization is achieved if there is an observed reduction in illness (for example, less weight loss, reduction in symptoms, reduction in lung pathology), reduction in viral titers, and/or protection from death.

Examples of subjects that can be administered the disclosed inactivated influenza virus compositions include subjects that can be (or are) infected with influenza. Examples of such subjects include but are not limited to, mammalian and avian subjects, such as humans, pigs, chickens, turkeys, horses, dogs and cats. Human subjects can be either adult (including elderly) or pediatric subjects.

In some embodiments of the methods of eliciting an immune response or immunizing a subject, the subject is administered (such as intranasally or intramuscularly) about 1 to about 25 μg of each of the at least four different inactivated viruses in the composition. In particular examples, the subject is administered (for example, intranasally or intramuscularly) about 1 to about 5 μg of each of the at least four different inactivated viruses in the composition, about 5 to about 20 μg of each of the at least four different inactivated viruses in the composition, or about 10 to about 15 μg of each of the at least four different inactivated viruses in the composition. In one specific non-limiting example, the subject is administered (for example, intranasally or intramuscularly) about 1.5 μg or 15 μg of each of the at least four different inactivated viruses in the composition. However, one of skill in the art is capable of determining a therapeutically effective amount (for example an amount that provides protection against H1N1 influenza virus infection) of inactivated virus to administer to a subject.

A. Methods of Administration

The disclosed inactivated influenza virus-containing compositions can be administered to a subject by any of the routes normally used for introducing viruses into a subject. Methods of administration include, but are not limited to, intradermal, intramuscular, intraperitoneal, parenteral, intravenous, subcutaneous, mucosal, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, tablets, and the like. Administration can be systemic or local.

The inactivated influenza virus-containing compositions administered to a subject are administered with at least one pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present disclosure. Pharmaceutically acceptable carriers include, but are not limited to, saline, buffered saline, dextrose, water, glycerol, sesame oil, ethanol, and combinations thereof. The composition can also contain conventional pharmaceutical adjunct materials such as, pharmaceutically acceptable salts to adjust the osmotic pressure, buffers, preservatives and the like. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

In particular examples, the compositions provided herein are formulated for mucosal vaccination, such as oral, intranasal, pulmonary, rectal and vaginal. In a specific example, this is achieved by intranasal administration. For example, the disclosed compositions can include one or more biodegradable, mucoadhesive polymeric carriers. Polymers such as polylactide-co-glycolide (PLGA), chitosan (for example in the form of chitosan nanoparticles, such as N-trimethyl chitosan (TMC)-based nanoparticles), alginate (such as sodium alginate) and carbopol can be included. In one example the composition includes one or more hydrophilic polymers, such as sodium alginate or carbopol. In one example, the composition includes carbopol, for example in combination with starch. In one example, the composition is formulated as a particulate delivery system used for nasal administration. Thus, the inactivated influenza virus-containing composition can include liposomes, immune-stimulating complexes (ISCOMs) and/or polymeric particles, such as virosomes. The inactivated influenza virus-containing compositions can also include one or more lipopeptides of bacterial origin, or their synthetic derivatives, such as Pam3Cys, (Pam2Cys, single/multiple-chain palmitic acids and lipoamino acids (LAAs). The compositions can also include one or more adjuvants, such as one or more of CpG oligodeoxynucleotides (CpG ODN), Flt3 ligand, and monophosphoryl lipid A (MLA). In one example, the adjuvant includes a clinical grade MLA formulation, such as MPL® (3-O-desacyl-4'-monophosphoryl lipid A) adjuvant.

B. Timing of Administration

The disclosed compositions containing four or more inactivated influenza viruses are administered as a single dose or as multiple doses (for example, boosters). In some examples, the first administration is followed by a second administration. For example, the second administration can be with the same, or with a different inactivated influenza virus-containing composition than the first inactivated influenza virus-containing composition administered. In a specific example, the second administration is with the same inactivated influenza virus-containing composition as the first inactivated influenza virus-containing composition administered. In another specific example, the second administration is with a different inactivated influenza virus-containing composition than the first inactivated influenza virus-containing composition administered. For example, if the first inactivated influenza virus-containing composition included a first HA subtype, a second HA subtype, a third HA subtype and a fourth HA subtype, the second inactivated influenza virus-containing composition can include a fifth HA subtype, a sixth HA subtype, a seventh HA subtype and an eighth HA subtype, wherein all eight subtypes are different.

In some examples, the compositions containing four or more inactivated influenza viruses are administered as multiple doses, such as 2, 3, 4, 5, 6, 7, 8, 9 or 10 doses (such as 2-3 doses). In such examples, the timing between the doses can be at least 1 week, at least 2 weeks, at least 3 weeks, at least 4 weeks, at least 6 weeks, at least 8 weeks, at least 12 weeks, at least 2 months, at least 3 months, at least 4 months, at least 5 months, at least 6 months, at least 1 year, at least 2 years, at least 5 years or at least 10 years, such as 1-4 weeks, 2-3 weeks, 1-6 months, 2-4 months, 1-10 years, or 2-5 years, or combinations thereof (such as where there are at least three administrations, wherein the timing between the first and second, and second and third doses, can be the same or different).

C. Dosages

The dose administered to a subject in the context of the present disclosure should be sufficient to induce a beneficial therapeutic response in a subject over time, or to inhibit or prevent influenza virus infection. The dose required can vary from subject to subject depending on the species, age, weight and general condition of the subject, the severity of the infection being treated, the particular composition being used and its mode of administration. An appropriate dose can be determined by one of ordinary skill in the art using only routine experimentation.

In some embodiments, the subject is administered (for example, intranasally or intramuscularly) about 1 to about 100 μg of each of the at least four different inactivated viruses in the composition, such as about 1 μg to about 50 μg, 1 μg to about 25 μg, 1 μg to about 5 μg, about 5 μg to about 20 lag, or about 10 μg to about 15 μg of each of the at least four different inactivated viruses in the composition. In one specific non-limiting example, the subject is administered (for example, intranasally or intramuscularly) about 15 μg of each of the at least four different inactivated viruses in the composition. In another specific non-limiting example, the subject is administered (for example, intranasally or intramuscularly) about 10 μg of each of the at least four different inactivated viruses in the composition. In one specific non-limiting example, the subject is administered (for example, intranasally or intramuscularly) about 20 μg of each of the at least four different inactivated viruses in the composition. In one specific non-limiting example, the subject is administered (for example, intranasally or intramuscularly) about 1 μg or 2 μg of each of the at least four different inactivated viruses in the composition.

D. Methods for Measuring an Immune Response

Methods for determining whether an inactivated influenza virus-containing composition disclosed herein can or did elicit or stimulate an immune response, such as achieve a successful immunization, are known in the art. For example, see Cottey et al., in *Current Contents in Immunology* 19.11.1-19.11.32, 2001 (herein incorporated by reference). Although exemplary assays are provided herein, the disclosure is not limited to the use of specific assays.

Following administration of an inactivated influenza virus composition provided herein, one or more assays can be performed to assess the resulting immune response. In some example, the assays are also performed prior to administration of the composition, to serve as a baseline or control. Samples are collected from the subject following administration of the composition, such as a blood or serum sample. In some examples, the sample is collected at least 1 week, at least 2 weeks, at least 3 weeks, at least 4 weeks, at least 5 weeks, at least 6 weeks or at least 8 weeks (such as 1, 2, 3, 4, 5, 6, 7, 8, 9, 10, 11 or 12 weeks) after the first administration. Subsequent samples can be obtained as well, for example following subsequent administrations.

1. Hemagglutination Titer Assay

Hemagglutination titer assays can be performed to measure or evaluate hemagglutinating units (HAU). This assay can be used to evaluate whether a virus expresses functional HA trimers, and can also be used to quantify HA protein in a virus preparation. Hemagglutination titers are also used to quantify the amount of influenza virus used as a challenge virus, or for example to quantify the amount of virus present in the lungs or respiratory tract of challenged animals. Vaccinated subjects may show a reduction in viral titers as compared to mock-vaccinated subjects.

This assay can be used to quantify the amount of virus in a sample, such as a lung sample from a virus challenged subject previously administered the inactivated influenza virus-containing compositions provided herein. Virus stocks are serially diluted (for example, 2-fold from 1:4 to 1:4096) and then added to wells containing red blood cells (RBCs). RBC solution (such as 0.75% to 1% RBC) is added to the wells. The mixture is then incubated for 30 minutes at room temperature, which allows the RBC to settle. The samples are then analyzed for their resulting agglutination pattern, for example by examining microtiter wells in which the sample was placed. For example, in a microtiter plate placed on its edge, the RBC in the RBC control wells will flow into a characteristic teardrop shape (no influenza virus is present so there is no agglutination). Wells that contain influenza virus will agglutinate the RBC to varying degrees. The wells with the greatest amount of virus will appear cloudy, because the virus has cross-linked all the red blood cells, preventing their pelleting. Lesser amounts of virus in succeeding wells may result in partial agglutination, but the pellet will not stream into a teardrop shape similar to the pellets in the RBC control wells. The endpoint is typically determined as the greatest dilution of the virus sample resulting in complete agglutination of the RBC.

The number of HAU in the sample being titered can be determined. The HA titer is the reciprocal of the dilution of the last well of a series showing complete agglutination of the RBC (for example, if the last dilution was 1:640, the titer of the sample is 640 HA units/5 μl sample).

2. Hemagglutination Inhibition (HAI) Assay

In one example, following administration of an inactivated influenza virus-containing composition provided herein, a hemagglutination inhibition (HAI), assay is performed. Influenza viruses can agglutinate red blood cells, a process called hemagglutination, as described above. In the presence of specific antibody to the surface hemagglutinin, hemagglutination is blocked. This phenomenon provides the basis for the HAI assay, which is used to detect and quantitate specific antiviral antibodies in serum. Thus, HAI measures the presence of antibodies that block HA receptor binding (as assessed by hemagglutination of RBC).

In one example, sera to be evaluated for the presence of antibodies against the head of hemagglutinin is treated with receptor destroying enzyme (RDE) at 37° C. overnight. The following day, RDE is inactivated by incubation at 56° C. for 1 hour. Assay plates used are 96-well, nonsterile, non-tissue culture-treated, round-bottom microtiter plates. Two-fold serial dilutions are carried out on each sample down the plate from row B through row G. Fifty μl of working dilution of viral antigen (a set number of HAU) is added to all wells of the microtiter plates except for row H (the RBC control wells) and the antigen control wells. The plates are incubated for 30 minutes at room temperature. Fifty μl 1% RBC suspension in PBS is added to all wells and the plates are incubated for 30 to 45 minutes at room temperature. The microtiter plate is analyzed to read the agglutination patterns. The negative control wells (those containing normal serum without anti-influenza antibodies) will appear cloudy, because the influenza virus has completely agglutinated the RBC. The positive control wells (those containing known anti-influenza antiserum) will have RBC pellets similar in appearance to the row H control pellets as long as there is sufficient anti-influenza antibody to inhibit agglutination. With increasing serum dilution, the amount of antibody will decrease so that increasing amounts of RBC agglutination will become apparent. The hemagglutination inhibition (HAI) titer for each serum sample is the reciprocal of the greatest dilution which completely inhibits the agglutination of the RBC (i.e., the last well in a dilution series forming a RBC pellet). The HAI titer for each sample is the mean of the endpoint titers of its duplicate dilution series. If the titer of the duplicates differs by more than one two-fold dilution, the HAI titer can be repeated for that sample.

3. Influenza Virus Neutralization Assay

In one example, following administration of a composition provided herein, a neutralization assay is performed. In this assay, serum samples from subjects who received an inactivated influenza virus-containing composition provided herein are diluted, influenza virus is added, and the amount of serum necessary to prevent virus growth determined. Neutralization assesses the presence of antibodies that inhibit viral replication. Antibodies to the stalk of HA for example can neutralize viral replication but not affect hemagglutination because the epitope is not around the receptor binding domain. Antibodies that bind to the head and inhibit hemagglutination are usually neutralizing.

In some examples, the serum samples are incubated in tissue culture medium (such as DMEM/5% FBS containing antibiotics), for example in 96-well, round-bottom, tissue culture-treated microtiter plate. The serum samples are serially diluted, for example in duplicate adjacent wells of a microwell plate (for example initially diluted 1:10 to a dilution of the sample of 1:640). Previously titered influenza virus (of any subtype) can be diluted to contain 1 $TCID_{50}$/50 Equal amounts of the working stock virus (such as about 50 $TCID_{50}$) are added to each serum sample (including the serial dilutions), and incubated at 37° C. for 1 hour. With this protocol, the same neutralization titer is obtained if the final amount of virus is between 10 to 100 $TCID_{50}$. Following the incubation, tissue culture medium (such as DMEM/5% FBS with antibiotics) containing $2.5\times10^5$ MDCK cells/ml (or other cells) are added to the serum samples (for example, to all wells of the microtiter plate). This is incubated overnight in a humidified 37° C., 5% $CO_2$ incubator. Some influenza viruses will grow better at temperatures of 34° to 35° C., and thus in some examples those temperatures are used. The media is removed, and replaced with tissue culture medium (such as DMEM with antibiotics) containing trypsin (such as 0.0002%), and the mixture is incubated in a humidified 37° C., 5% $CO_2$ incubator for 4 days. Subsequently, sterile 0.5% RBC/PBS solution is added, and the mixture incubated at 4° C. for 1 hour, and the wells are checked for the presence of agglutination. The virus neutralization titer of a particular serum sample is defined as the reciprocal of the highest dilution of serum where both wells show no agglutination of the RBC.

Samples (for example, in a microwell) containing influenza virus neutralizing antibodies at sufficient concentration will prevent the virus from infecting the cells so that viral multiplication will not take place. The addition of RBCs to these wells will result in the formation of a pellet of RBC. In contrast, samples (for example, in a microwell) that had none or less than neutralizing concentrations of anti-influenza antibody will have influenza virus present at the end of the 4-day incubation. The RBC added to these samples will agglutinate. Influenza virus cross-links the red blood cells, inhibiting their settling in the microwell, and the wells therefore appear cloudy.

4. Neuraminidase Inhibiting (NI) Antibody Titer Assay

Neuraminidase inhibiting (NI) antibody titers can also be determined. To measure NI antibody titers, reassortant viruses containing the appropriate NA can be generated, for example by using plasmid-based reverse genetics (for example, see Sandbulte et al., *Influenza Other Respir Viruses* 3:233-40, 2009). The appropriate NA will be the same one(s) present in the viruses administered to the subject. The NI assay can be performed using fetuin as a NA substrate (for example, see Cate et al., *Vaccine* 28:2076-9, 2010, herein incorporated by reference). An exemplary method is provided below.

The NI titer is the inverse of the greatest dilution of sera that provides at least 50% inhibition of NA activity. It is expected that use of the compositions disclosed herein will decrease or even eliminate challenge virus titers in subjects who received the inactivated influenza virus compositions. For example, subjects who receive the inactivated influenza virus compositions are expected to have at least 10-fold, at least 20-fold, at least 50-fold, or even 100-fold less virus in the lungs than subjects who did not receive the inactivated influenza virus compositions (for example, are mock vaccinated).

NI antibody titers can be determined in an enzyme-linked lectin assay using peroxidase-labeled peanut agglutinin (PNA-PO) to bind to desialylated fetuin. NA activity can be determined by incubating serial dilutions of purified, full length NA on fetuin coated microtiter plates. After 30 minutes of incubation at RT, plates are washed and PNA-PO added. After a one-hour incubation at RT, plates are again washed and the peroxidase substrate 3,3',5,5'-tetramethylbenzidine is added and color development is allowed to proceed for 10 minutes. Color development is stopped and the plates OD450 is measured. Dilution corresponding to 95% NA activity is determined.

NI titers against an NA subtype can be measured beginning at a 1:20 dilution of sera followed by 2-fold serial dilutions in 96-well U-bottomed tissue culture plates. NAs corresponding to 95% maximum activity are added to diluted sera and incubated for 30 minutes at RT after which sera/NA samples were transferred to fetuin coated microtiter plates. Plates are incubated for 2 hours at 37° C., washed and PNA-PO added. The plates are incubated at RT an additional hour, washed and peroxidase substrate TMB is added. Color development is stopped after 10 minutes and the OD450 of the plates is measured. The NI titers are the reciprocal dilution at which 50% NA activity was inhibited. The lower limit of quantitation for the assay is 20; titers lower than 20 are considered to be negative and assigned a value of 10. In some examples a good or positive response produces a value of >30, while a poor or no response produces a value <20.

5. Viral Lung Titers and Pathology

Viral lung titers and pathology can be determined. Tissue samples, such as lung samples (for example, inflated lung samples) are fixed (for example, 24 hour fixation in 10% formaldehyde), embedded (for example, in paraffin), cut into sections (for example, 1 to 10 μm, such as 5 μm), and mounted.

Influenza virus antigen distribution can be evaluated by immunohistochemistry using an appropriate antibody (for example, a polyclonal or monoclonal antibody that is either specific for the virus used to challenge the subject or one that is cross-reactive to different influenza virus strains can be used). It is expected that use of the compositions disclosed herein will decrease or even eliminate virus titers in subjects who received the inactivated influenza virus compositions. For example, subjects who receive the inactivated influenza virus compositions are expected to have at least 10-fold, at least 20-fold, at least 50-fold, or even 100-fold less virus in the lungs than subjects who did not receive the inactivated influenza virus compositions (for example, are mock vaccinated). In another example, it is expected that use of the compositions disclosed herein will decrease or even eliminate symptoms of influenza infection, such as bronchitis, bronchiolitis, alveolitis, and/or pulmonary edema, in subjects who received the compositions. For example, subjects who receive the inactivated influenza virus compositions are expected to have at least 20%, at least 50%, at least 75%, or at least 90% less bronchitis, bronchiolitis, alveolitis, and/or pulmonary edema (or such reductions in severity of these symptoms) as compared subjects who did not receive the inactivated influenza virus compositions (for example, are mock vaccinated).

6. Other Exemplary Assays

In some examples, subjects are assessed for respiratory IgA and systemic IgG, T-cell responses. Such methods are routine (for example, see Gauger et al., *Methods Mol Biol.* 1161:303-12, 2014; Larsen et al., *Vet Microbiol.* 74(1-2): 117-31, 2000; Steitz et al., *PLoS One.* 5(5):e10492, 2010).

In some examples, immune responses are analyzed by transcriptomics and cytokine ELISAs or other cytokine immunoassays. Such methods are routine.

In some examples, immune responses are analyzed by microneutralization. Such methods are routine (for example, see Gauger et al., *Methods Mol Biol.* 1161:313-24, 2014).

In some examples, immune responses are analyzed by anti-HA stalk assays. Such methods are routine (for example, Wu et al., *PLoS One* 7(8):e42363, 2012).

The following examples are provided to illustrate certain particular features and/or embodiments. These examples should not be construed to limit the disclosure to the particular features or embodiments described.

EXAMPLES

Example 1: Cocktail of Chemically Inactivated Influenza Viruses as a Universal Influenza Vaccine This example describes studies to evaluate influenza virus vaccines comprised of a cocktail of BPL-inactivated low pathogenicity avian influenza virus subtypes. A first vaccine cocktail includes influenza viruses with HA subtypes H1, H3, H5 and H7, and a second vaccine cocktail includes influenza viruses with HA subtypes H2, H4, H9 and H10 (see FIG. 3). The influenza viruses used in the assay were monovalent (e.g., included only a single or individual HA subtype.

A tetravalent vaccine consisting of four different BPL-inactivated whole influenza viruses (A/mallard/Ohio/265/1987 (H1N9), A/pintail/Ohio/339/1987 (H3N8), A/mallard/Maryland/802/2007 (H5N1) and A/Environment/Maryland/261/2006 (H7N3)) was compared to a virus-like particle (VLP) vaccine comprised of VLPs expressing HA from the same viruses. FIG. 1 shows reciprocal HAI titers of mice vaccinated with the tetravalent influenza VLP vaccine or with the BPL-inactivated whole virus tetravalent influenza virus vaccine. Titers against H1N1, H3N8, H5N1 and H7N3 are shown. The results demonstrate that both vaccines elicited a broad, heterosubtypic immune response.

Figure 2A:
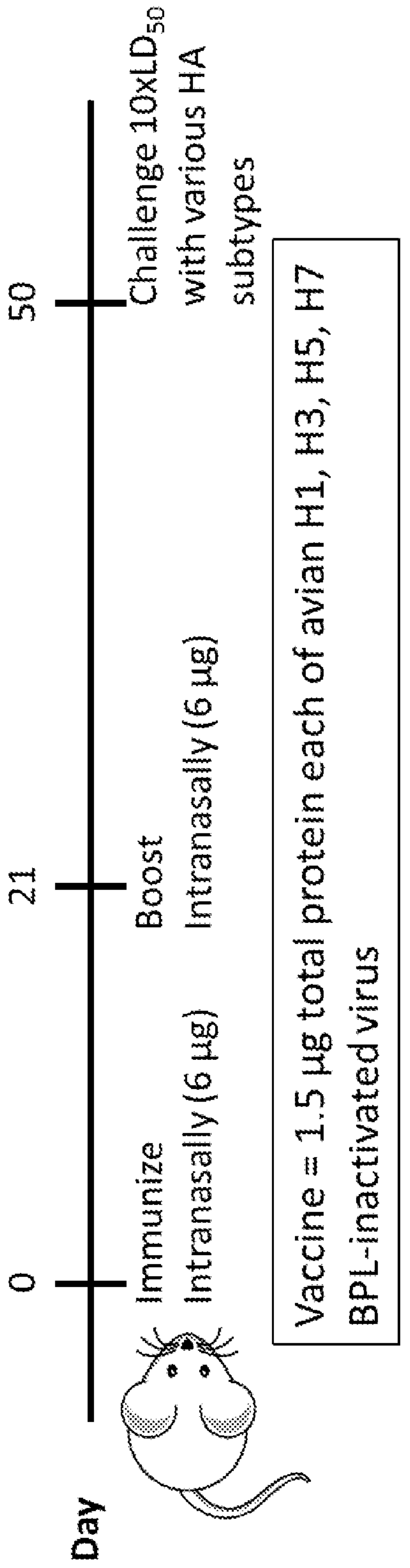
FIG. 2A is a schematic illustrating the timeline for vaccinating mice with a BPL-inactivated, low pathogenicity avian influenza virus cocktail. Mice were intranasally (IN) or intramuscularly (IM) inoculated with a mixture of four different BPL-inactivated influenza viruses, each expressing a different avian HA (H1, H3, H5 or H7). Mice were boosted 3 weeks (21 days) after the initial immunization and challenged at 6 weeks (50 days) with a variety of influenza viruses of different subtypes.
Figure 2B:
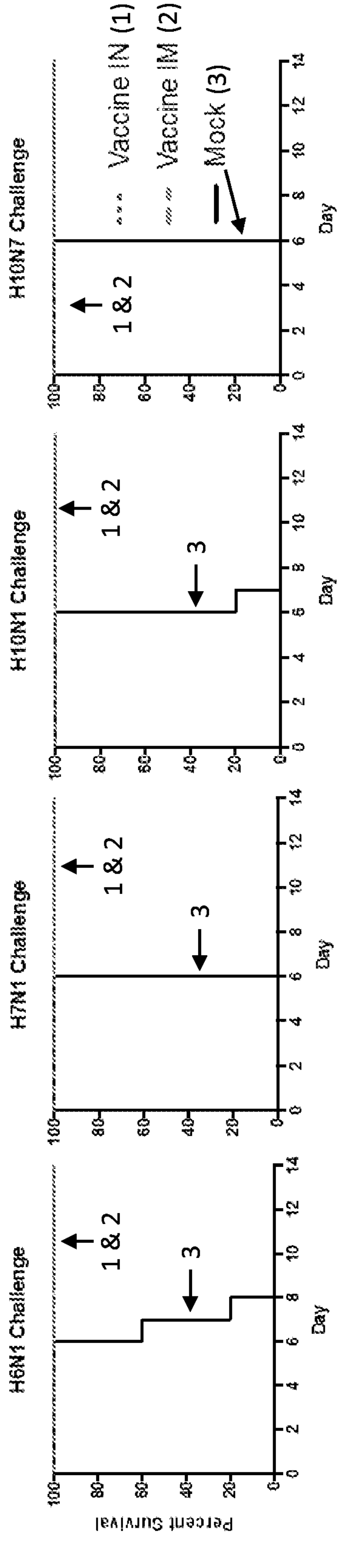
FIG. 2B is a series of graphs showing survival of vaccinated mice challenged with either H6N1, H7N1, H10N1 or H10N7 influenza virus. All mice vaccinated either IN or IM survived challenge by each influenza virus, while mock-vaccinated mice succumbed 6-8 days following challenge.

The ability of the BPL-inactivated influenza virus vaccine to provide protection against influenza virus challenge was evaluated in mice. Mice were inoculated intramuscularly (IM) or intranasally (IN) with the BPL-inactivated vaccine and boosted three weeks later (FIG. 2A). Vaccinated mice were challenged 50 days after the first immunization with either H6N1, H7N1, H10N1 or H10N7 influenza virus. As shown in FIG. 2B, all mice vaccinated either IN or IM survived challenge by each influenza virus, while mock-vaccinated mice succumbed 6-8 days following challenge.

Another study was performed to evaluate the immune response elicited by a second vaccine cocktail consisting of four different BPL-inactivated whole influenza viruses (A/green-winged teal/Ohio/175/1986 (H2N1), A/green-winged teal/Ohio/344/1986 (H4N2), A/Mallard/Maryland/798/2007 (H9N1) and A/Mallard/Ohio/99/1989 (H10N7)). Mice were vaccinated with the H2/H4/H9/H10 tetravalent vaccine and reciprocal HAI titers against H1N1, H6N1, H7N1 and H15N1 were determined. The results demonstrated that the H2/H4/H9/H10 tetravalent vaccine elicited a broad, heterosubtypic immune response.

Figure 4A:
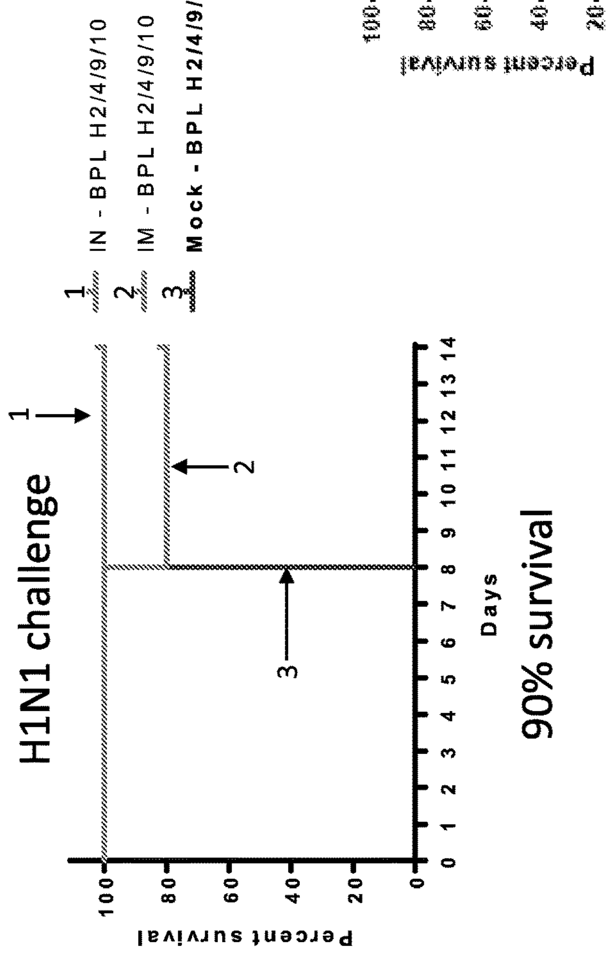
FIGS. 4A-4E are a series of graphs showing survival of mice that were mock-vaccinated, IN vaccinated or IM vaccinated with a tetravalent (H2/H4/H9/H10) BPL-inactivated influenza virus vaccine and challenged with heterotypic viruses H1N1 (FIG. 4A), H6N1 (FIG. 4B), H7N1 (FIG. 4C) and H15N1 (FIG. 4D), or homotypic virus H10N1 (FIG. 4E).
Figure 4B:
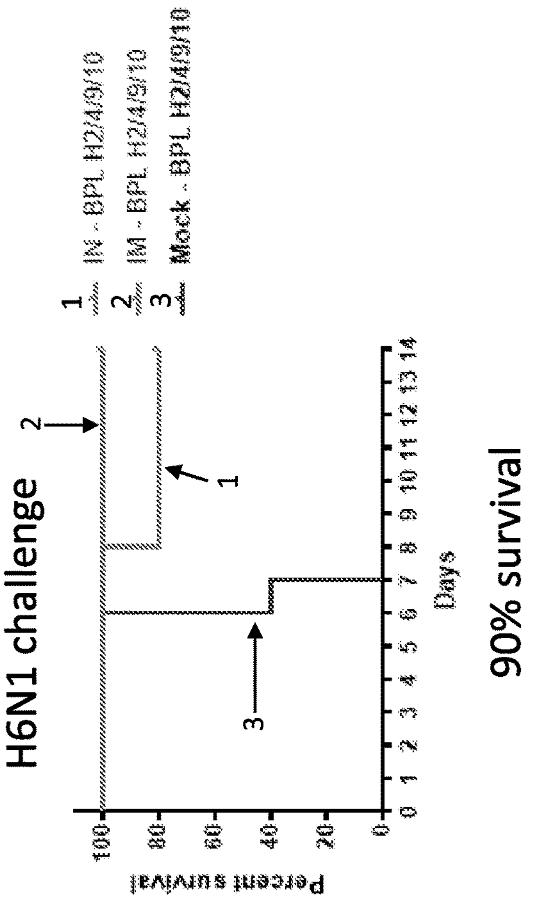
Figure 4C:
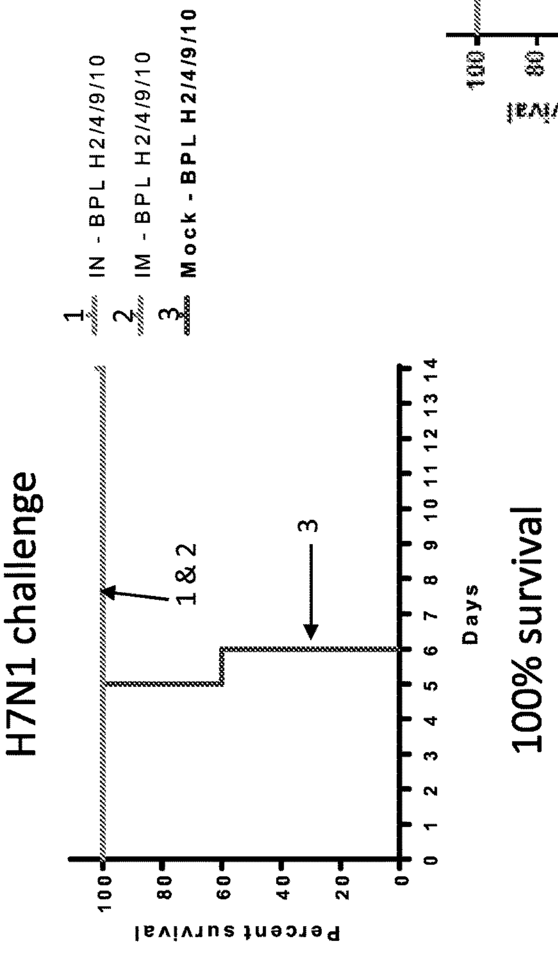
Figure 4D:
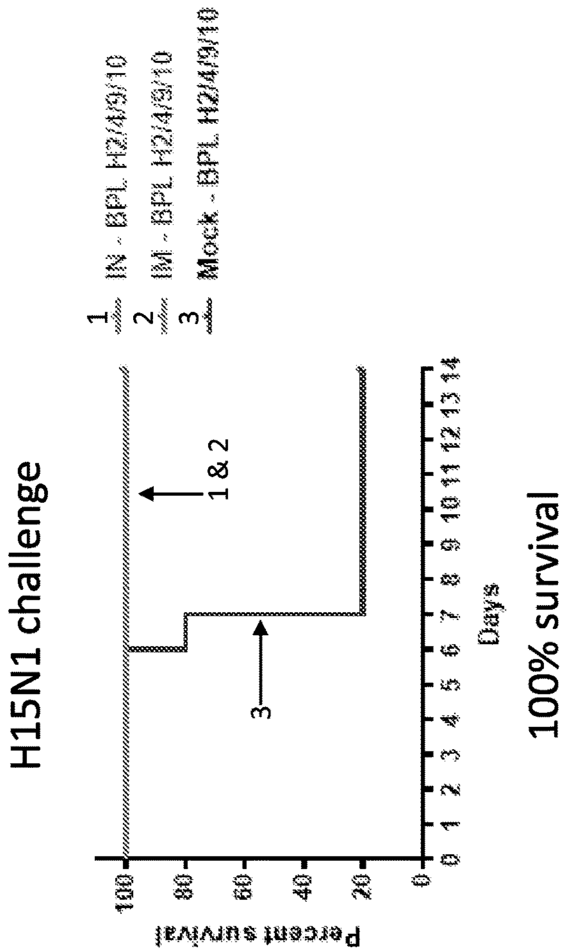
Figure 4E:
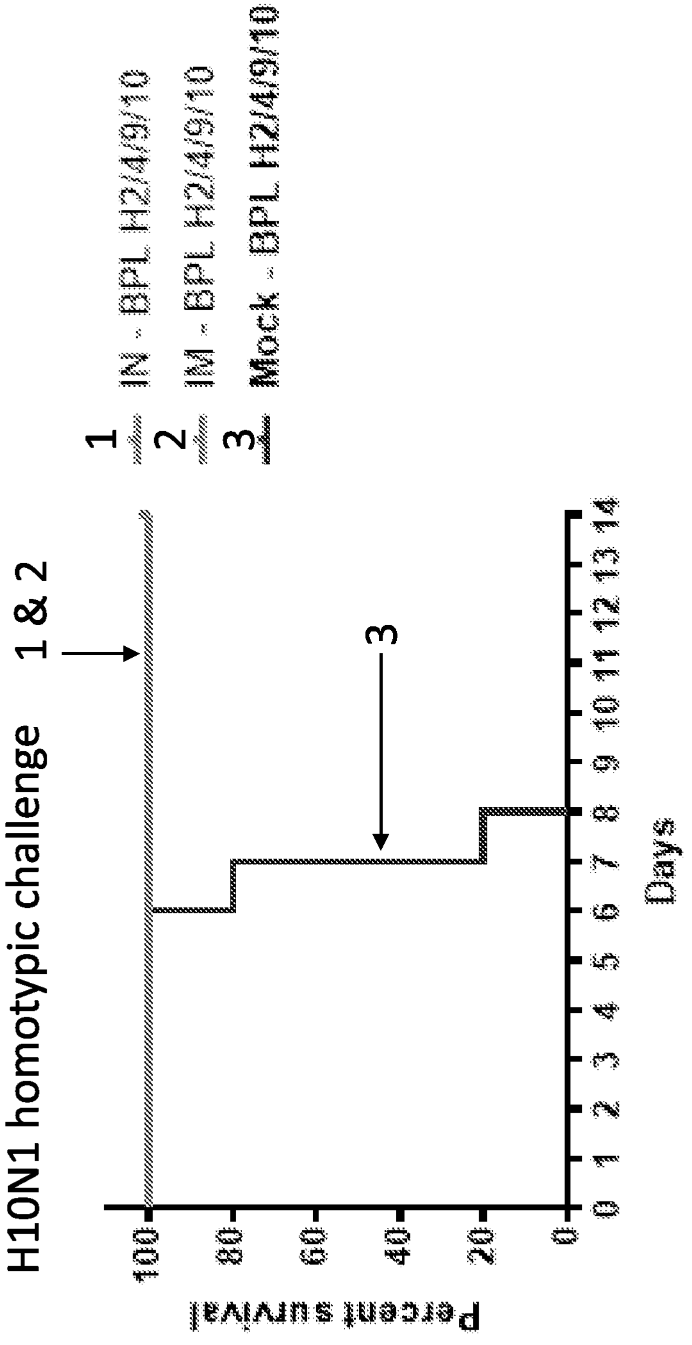

The ability of the BPL-inactivated H2/H4/H9/H10 tetravalent influenza virus vaccine to provide protection against influenza virus challenge was also evaluated in mice. Mice were mock-vaccinated or inoculated IM or IN with the H2/H4/H9/H10 tetravalent vaccine and boosted three weeks later. Vaccinated mice were challenged 50 days after the first immunization with either H1N1, H6N1, H7N1 or H15N1 influenza virus. Vaccinated mice exhibited 90% survival against H1 and H6 challenge (FIGS. 4A and 4B), and 100% survival against H7 and H15 challenge (FIGS. 4C and 4D). Vaccination (IN or IM) also conferred 100% protection against homotypic virus (H10N1) challenge (FIG. 4E).

An additional study is performed to evaluate the immune response elicited by a vaccine cocktail consisting of eight different BPL-inactivated whole influenza viruses (A/mallard/Ohio/265/1987 (H1N9), A/pintail/Ohio/339/1987 (H3N8), A/mallard/Maryland/802/2007 (H5N1), A/Environment/Maryland/261/2006 (H7N3), A/green-winged teal/Ohio/175/1986 (H2N1), A/green-winged teal/Ohio/344/1986 (H4N2), A/Mallard/Maryland/798/2007 (H9N1) and A/Mallard/Ohio/99/1989 (H10N7)). Mice are vaccinated with the H1/H3/H5/H7/H2/H4/H9/H10 octavalent vaccine and reciprocal HAI titers against H1N1, H3N8, H5N1 and H7N3 (and/or other influenza viruses) are determined. It is expected that the octavalent vaccine will elicit a broad, heterosubtypic immune response.

The ability of the BPL-inactivated H1/H3/H5/H7/H2/H4/H9/H10 octavalent vaccine to provide protection against influenza virus challenge is evaluated in mice. Mice are inoculated IM or IN with the octavalent vaccine and boosted three weeks later. Vaccinated mice are challenged 50 days after the first immunization with either H2N2, H6N1, H11N1, or H15N1 influenza virus. It is expected that mice vaccinated either IN or IM will survive challenge by each influenza virus.

Example 2: Inactivated Influenza Virus Vaccine Testing in Ferrets

Fitch ferrets (*Mustela putorius furo*, female, 6-12-months of age), influenza nave and de-scented, were purchased from Marshall Farms (Sayre, Pa., USA). Ferrets were pair housed in stainless steel cages (Shor-line, Kansas City, Kans., USA) containing Sani-chips Laboratory Animal Bedding (P. J. Murphy Forest Products, Montville, N.J., USA). Ferrets were provided with Teklad Global Ferret Diet (Harlan Teklad, Madison, Wis., USA) and fresh water ad libitum.

Figure 5A:
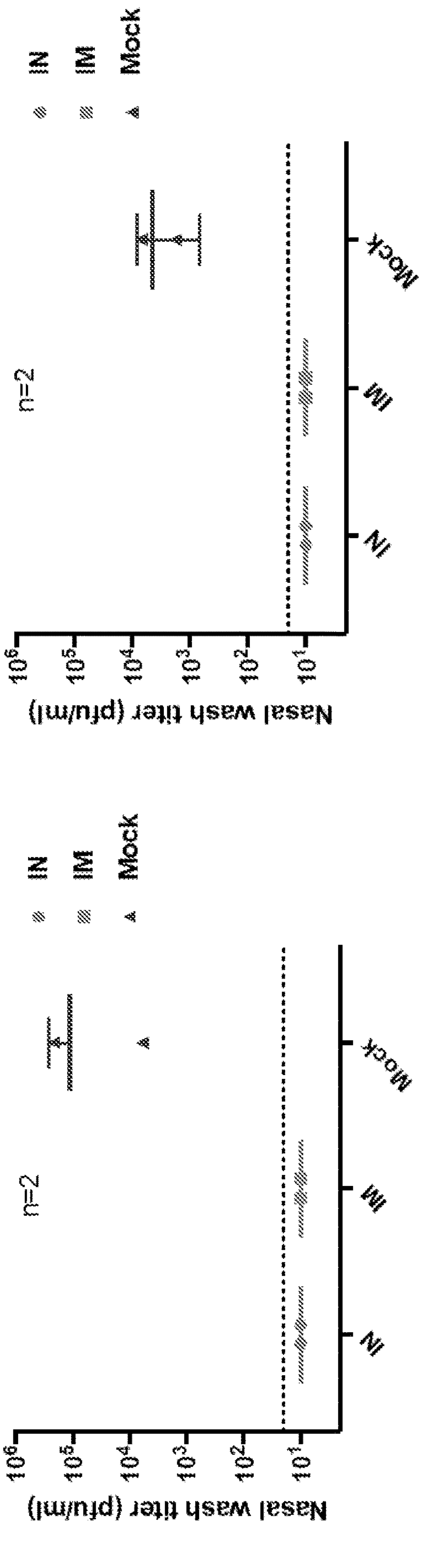
FIG. 5A is a pair of graphs showing nasal titers five days after ferrets vaccinated IN or IM with a BPL-inactivated tetravalent (H1/H3/H5/H7) influenza virus vaccine were challenged with pathogenic strain A/Port Chalmers/1971 (H3N2) (left) or A/swine/Iowa/1931 (H1N1) (right).
Figure 5B:
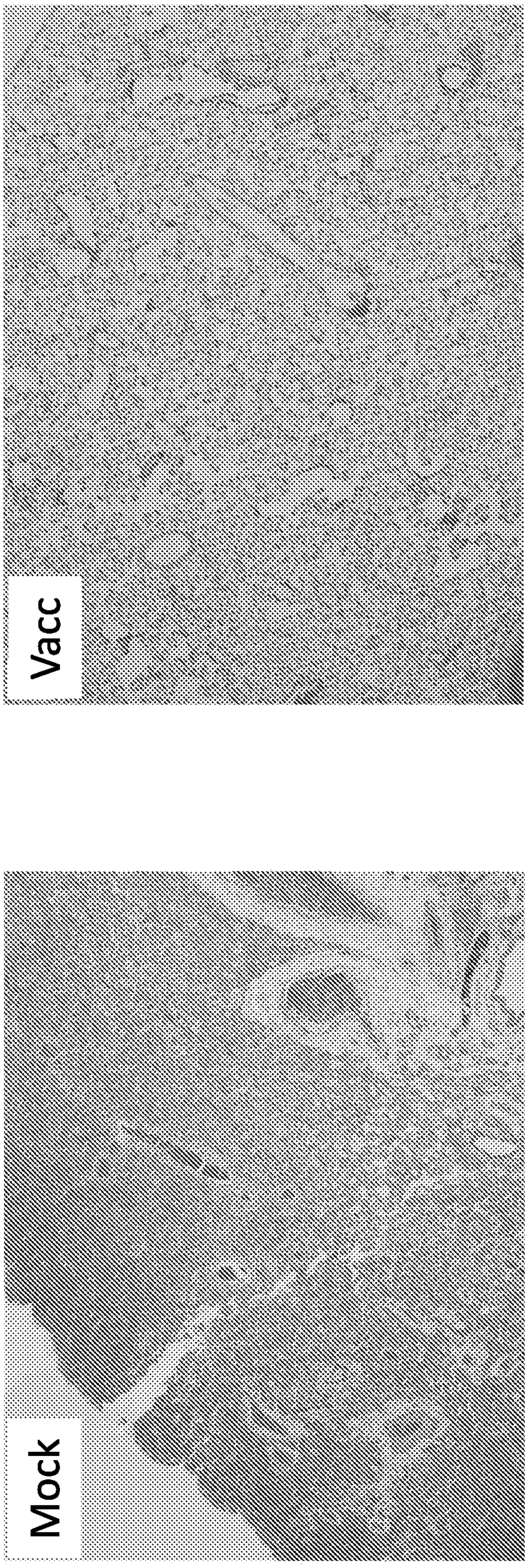
FIG. 5B shows lung pathology of the vaccinated and challenged ferrets as described in FIG. 5A.

Ferrets were mock-vaccinated or vaccinated IN or IM with a tetravalent vaccine consisting of four different BPL-inactivated whole influenza viruses: A/mallard/Ohio/265/1987 (H1N9), A/pintail/Ohio/339/1987 (H3N8), A/mallard/Maryland/802/2007 (H5N1) and A/Environment/Maryland/261/2006 (H7N3). Two ferrets were included in each vaccination group. Ferrets were challenged 4 weeks after vaccination with antigenically variant and pathogenic virus strains, A/Port Chalmers/1971 (H3N2) and A/swine/Iowa/1931 (H1N1). Vaccinated ferrets were afforded significant protection against challenge with both strains. In both cases, vaccinated animals showed $10^3$ to $10^4$ log reductions in viral nasal wash titers at day 5 compared to mock-vaccinated animals (FIG. 5A) and showed significantly less lung pathology (FIG. 5B).

In an additional experiment, ferrets vaccinated with the tetravalent H1/H3/H5/H7 vaccine were challenged with H2 and H10 influenza viruses to evaluate heterosubtypic protection in vaccinated ferrets. It was determined that ferrets vaccinated with the tetravalent vaccine lost less weight than mock-vaccinated animals. It is expected that vaccinated animals also will have lower virus titers in lung and nasal wash samples.

In additional studies, ferrets are IN administered two doses of an inactivated influenza virus vaccine (such as tetravalent H1/H3/H5/H7, tetravalent H2/H4/H9/H10 or octavalent H1/H3/H5/H7/H2/H4/H9/H10) at week 0 and then boosted with the same dose at week 3. Animals are monitored for adverse events including weight loss, temperature, decrease in activity, nasal discharge, sneezing and diarrhea weekly during the vaccination regimen. Prior to vaccination, animals are confirmed by HAI assay to be seronegative for circulating influenza A and influenza B viruses. Fourteen to twenty-one days after each vaccination, blood is collected from anesthetized ferrets via the anterior vena cava and transferred to a microfuge tube. Tubes are centrifuged and sera is removed and frozen at −80±5° C. The serum is analyzed for immune response, for example by HAI serum antibody titer.

One to three weeks after final vaccination, ferrets are challenged separately with a lethal dose (10×$MLD_{50}$) intranasally with a variety of pathogenic influenza virus including the 1918 H1N1, 1957 H2N2, 1968 H3N2, and 2009 H1N1 pandemic viruses, highly pathogenic H5N1, H7N9, and H6N1 avian influenza viruses, and other relevant challenge viruses. After infection, ferrets are monitored daily for weight loss, disease signs and death for 14 days after infection. Individual body weights, sickness scores, and death are recorded for each group on each day after inoculation. Nasal washes are performed by instilling 3 ml of PBS into the nares of anesthetized ferrets each day for 7 days after inoculation. Washes are collected and stored at −80° C. until use. Serum can also be collected.

Ferrets are evaluated for survival and vaccine-induced immunity, for example, by hemagglutination inhibition, microneutralization, and anti-HA stalk assays along with neuraminidase inhibition assays. Vaccinated animals are also assessed for respiratory IgA and systemic IgG, T-cell responses, viral lung titers and pathology, and immune responses by transcriptomics and cytokine ELISAs.

It is expected that the inactivated influenza virus cocktails will protect the ferrets from challenge with all of these viruses.

Example 3: Human Clinical Trials

After the selection of optimal broadly cross-reactive inactivated influenza virus vaccines in experimental animals, studies are conducted in human volunteers. In some examples, the vaccine will include an adjuvant suitable for human use.

An intranasal vaccine formulation that includes a cocktail of inactivated (such as BPL-inactivated) whole influenza virus will be generated using GMP methods (such as tetravalent H1/H3/H5/H7, tetravalent H2/H4/H9/H10 or octavalent H1/H3/H5/H7/H2/H4/H9/H10), and administered to humans intranasally. One skilled in the art will appreciate that other inactivated influenza virus vaccine compositions provided herein can be similarly tested.

Briefly, humans are vaccinated intranasally with an influenza vaccine composition. About 3-12 weeks later (such as 3, 4, 5, 6, 7, 8, 9, 10, 11, or 12 weeks later), the humans are boosted with the same mixture. A second group of humans are mock vaccinated (for example with saline). Blood and nasal samples are obtained and stored. Patients are monitored for any adverse events during the course of study. Since inactivated vaccines are not infectious, they are expected to have an excellent safety profile.

If the vaccine composition is shown to be safe in Phase I trials, Phase II efficacy trials are performed using a human volunteer influenza challenge model, as developed at the NIH Clinical Center (for example, see Memoli et al., Validation of a Wild-Type Influenza A Human Challenge Model: H1N1pdMIST, An A(H1N1)pdm09 Dose Finding IND Study). Subjects are screened for health status and by HAI assay for low titers (<1:10) against the challenge 2009 pandemic H1N1 virus. Screened patients enrolled in the study are intranasally vaccinated with the inactivated influenza virus vaccine (cohort 1) or given a mock vaccination with saline (cohort 2). They are boosted at three weeks, and then at six weeks their serologic titers are assessed by HAI or other assays, and the subjects are challenged with a dose of virus validated to induce influenza illness and shedding in >60% subjects pre-challenge HAI titers <1:10. Vaccine efficacy is assessed by development of serologic responses to vaccination, reduction in symptoms, reduction in viral titers, and/or reduction in duration of viral shedding.

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

The invention claimed is:

1. A composition comprising:

a first influenza A virus comprising a hemagglutinin (HA) of a first subtype;

a second influenza A virus comprising a HA of a second subtype;

a third influenza A virus comprising a HA of a third subtype; and a fourth influenza A virus comprising a HA of a fourth subtype, wherein at least one of the first, second, third and fourth HA subtypes are selected from H3, H4, H7, H10, H14 and H15, and/or at least one of the first, second, third and fourth HA subtypes are selected from H1, H2, H5, H6, H8, H9, H11, H12, H13 and H16, and wherein the first, second, third, and fourth influenza A viruses are inactivated.

2. The composition of claim 1, wherein at least one of the first, second, third and fourth HA subtypes are selected from H3, H4, H7, H10, H14 and H15.

3. The composition of claim 1, wherein at least two of the first, second, third and fourth HA subtypes are selected from H3, H4, H7, H10, H14 and H15.

4. The composition of claim 1, wherein at least one of the first, second, third and fourth HA subtypes are selected from H1, H2, H5, H6, H8, H9, H11, H12, H13 and H16.

5. The composition of claim 1, wherein at least two of the first, second, third and fourth HA subtypes are selected from H1, H2, H5, H6, H8, H9, H11, H12, H13 and H16.

6. The composition of claim 1, wherein the first, second, third and fourth HA subtypes are H1, H3, H5 and H7.

7. The composition of claim 1, wherein the first, second, third and fourth HA subtypes are H2, H4, H9 and H10.

8. The composition of claim 1, further comprising a fifth influenza A virus comprising a HA of a fifth subtype, wherein the fifth influenza A virus is inactivated.

9. The composition of claim 1, further comprising a sixth influenza A virus comprising a HA of a sixth subtype, wherein the sixth influenza A virus is inactivated.

10. The composition of claim 1, further comprising a seventh influenza A virus comprising a HA of a seventh subtype, wherein the seventh influenza A virus is inactivated.

11. The composition of claim 1, further comprising an eighth influenza A virus comprising a HA of an eighth subtype, wherein the eighth influenza A virus is inactivated.

12. The composition of claim 11, wherein the first, second, third, fourth fifth, sixth, seventh and/or eighth HA subtypes are selected from H1, H2, H3, H4, H5, H7, H9 and H10.

13. The composition of claim 1, wherein the influenza A viruses are chemically inactivated.

14. The composition of claim 13, wherein the influenza A viruses are chemically inactivated with beta-propiolactone (BPL).

15. The composition of claim 1, further comprising a pharmaceutically acceptable carrier.

16. The composition of claim 1, further comprising an adjuvant.

17. The composition of claim 1, formulated for intranasal administration.

18. The composition of claim 1, formulated for intramuscular administration.

19. A container comprising the composition of claim 1.

20. The container of claim 19, wherein the container is a syringe or a vial.

21. A method of eliciting an immune response to influenza virus in a subject, comprising administering a therapeutically effective amount of the composition of claim 1 to a subject, thereby eliciting an immune response to influenza virus in a subject.

22. A method of immunizing a subject against influenza virus, comprising administering to the subject a therapeutically effective amount of the composition of claim 1 to a subject, thereby immunizing the subject against influenza virus.

23. The method of claim 21, wherein the composition is administered intramuscularly.

24. The method of claim 21, wherein the composition is administered intranasally.

25. The method of claim 21, wherein the subject is a mammal or a bird.

26. The method of claim 21, wherein the subject is a human.

27. The method of claim 26, wherein the human is an adult subject.

28. The method of claim 26, wherein the human is a pediatric subject.

29. The method of claim 21, wherein the method provides a heterosubtypic immune response.

30. The method of claim 29, wherein:

the first, second, third and fourth HA subtypes are H1, H3, H5 and H7, and the heterosubtypic immune response confers at least partial protection against infection by influenza H2, H4, H6 and/or H10;

the first, second, third and fourth HA subtypes are H2, H4, H9 and H10, and the heterosubtypic immune response confers at least partial protection against infection by influenza H1, H3, H5, H6 and/or H7;

the first, second, third, fourth, fifth, sixth, seventh, and eighth HA subtypes are H1, H2, H3, H4, H5, H7, H9 and H10, and the heterosubtypic immune response confers at least partial protection against infection by influenza H6 and/or H8.

31. A kit comprising the container of claim 19.

32. The kit of claim 31, further comprising instructions for administration of the composition and/or a description of the components of the composition.

* * * * *